(12) United States Patent
Okada

(10) Patent No.: US 10,349,962 B2
(45) Date of Patent: Jul. 16, 2019

(54) ENDOSCOPE TREATMENT TOOL

(71) Applicant: OLYMPUS CORPORATION, Tokyo (JP)

(72) Inventor: Tsutomu Okada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/997,857

(22) Filed: Jun. 5, 2018

(65) Prior Publication Data

US 2018/0280042 A1 Oct. 4, 2018

Related U.S. Application Data

(63) Continuation of application No. PCT/JP2016/054561, filed on Feb. 17, 2016.

(51) Int. Cl.
| | |
|---|---|
| *A61B 17/221* | (2006.01) |
| *A61B 17/00* | (2006.01) |
| *A61B 17/22* | (2006.01) |

(52) U.S. Cl.
CPC ...... *A61B 17/221* (2013.01); *A61B 17/00234* (2013.01); *A61B 2017/00358* (2013.01); (Continued)

(58) Field of Classification Search
CPC .. A61B 17/22; A61B 17/22031–22032; A61B 17/221; A61B 2017/22034–22035; (Continued)

(56) References Cited

U.S. PATENT DOCUMENTS

| | | | |
|---|---|---|---|
| 4,347,846 | A | 9/1982 | Dormia |
| 6,093,196 | A | 7/2000 | Okada |
| | | (Continued) | |

FOREIGN PATENT DOCUMENTS

| | | |
|---|---|---|
| EP | 2638870 A1 | 9/2013 |
| EP | 3069667 A1 | 9/2016 |
| | (Continued) | |

OTHER PUBLICATIONS

International Search Report dated Apr. 5, 2016 issued in PCT/JP2016/054561.
(Continued)

*Primary Examiner* — Jonathan A Hollm
(74) *Attorney, Agent, or Firm* — Scully, Scott, Murphy & Presser, P.C.

(57) ABSTRACT

An endoscope treatment tool includes: a sheath having a lumen; a basket portion being configured to protrude from the lumen and formed of at least one elastic wire; and a manipulation wire causing the basket portion to be moved, wherein the elastic wire has a maximum-outer-diameter portion between distal and proximal ends of the elastic wire and a largest portion that, between the maximum-outer-diameter portion and the proximal end of the elastic wire, reaches the maximum size in an opposite direction from maximum-outer-diameter portion in a side view from a direction orthogonal to a perpendicular line drawn to a center axis from the maximum-outer-diameter portion, and wherein, in a front view of the basket portion, the largest portion is positioned on an opposite side from the side of the maximum-outer-diameter portion with respect to a straight line that is orthogonal to the perpendicular line on the center axis.

19 Claims, 24 Drawing Sheets

(52) U.S. Cl.
CPC ............ *A61B 2017/00818* (2013.01); *A61B 2017/00862* (2013.01); *A61B 2017/2212* (2013.01); *A61B 2017/2215* (2013.01); *A61B 2017/22062* (2013.01); *A61B 2017/22069* (2013.01)

(58) Field of Classification Search
CPC ....... A61B 2017/2212–2217; A61F 2/01–013; A61F 2002/011–018
See application file for complete search history.

(56) References Cited

U.S. PATENT DOCUMENTS

| | | | |
|---|---|---|---|
| 2003/0078605 | A1 | 4/2003 | Bashiri et al. |
| 2003/0153944 | A1 | 8/2003 | Phung et al. |
| 2004/0138692 | A1 | 7/2004 | Phung et al. |
| 2007/0239201 | A1 | 10/2007 | Phung et al. |
| 2010/0222806 | A1 | 9/2010 | Phung et al. |
| 2013/0211415 | A1* | 8/2013 | Zerfas .............. A61B 17/00234 606/114 |
| 2014/0012283 | A1* | 1/2014 | Yasuda ................ A61B 17/221 606/127 |
| 2016/0192957 | A1 | 7/2016 | Okada |
| 2016/0235423 | A1 | 8/2016 | Okada |

FOREIGN PATENT DOCUMENTS

| | | |
|---|---|---|
| EP | 3081177 A1 | 10/2016 |
| GB | 2066668 A | 7/1981 |
| GB | 2321192 A | 7/1998 |
| JP | S62-42617 B2 | 9/1987 |
| JP | H03-57214 Y2 | 12/1991 |
| JP | H10-192296 A | 7/1998 |
| JP | 3075355 B2 | 8/2000 |
| JP | 2005-506871 A | 3/2005 |
| JP | 2006-516212 A | 6/2006 |
| JP | 2015-123230 A | 7/2015 |
| WO | WO 03/034929 A1 | 5/2003 |
| WO | WO 2004/062513 A1 | 7/2004 |
| WO | WO 2012/141213 A1 | 10/2012 |
| WO | WO 2015/072366 A1 | 5/2015 |
| WO | WO 2015/087952 A1 | 6/2015 |

OTHER PUBLICATIONS

Japanese Office Action dated May 16, 2017 received in JP 2017-518362.

* cited by examiner

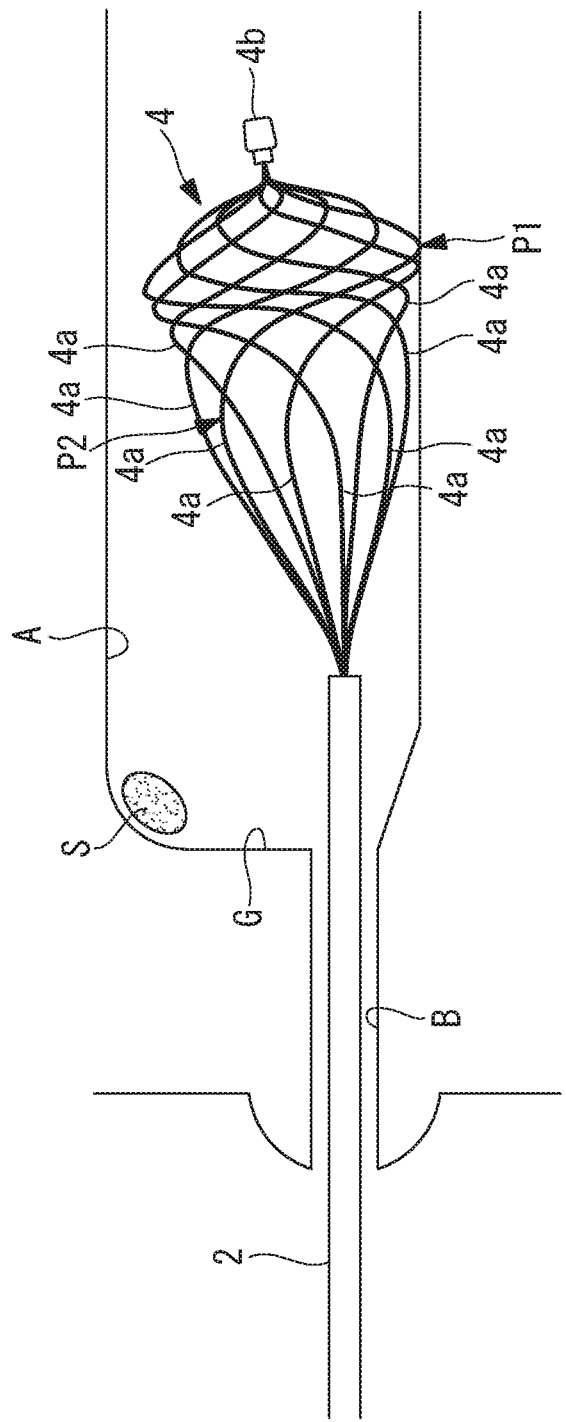

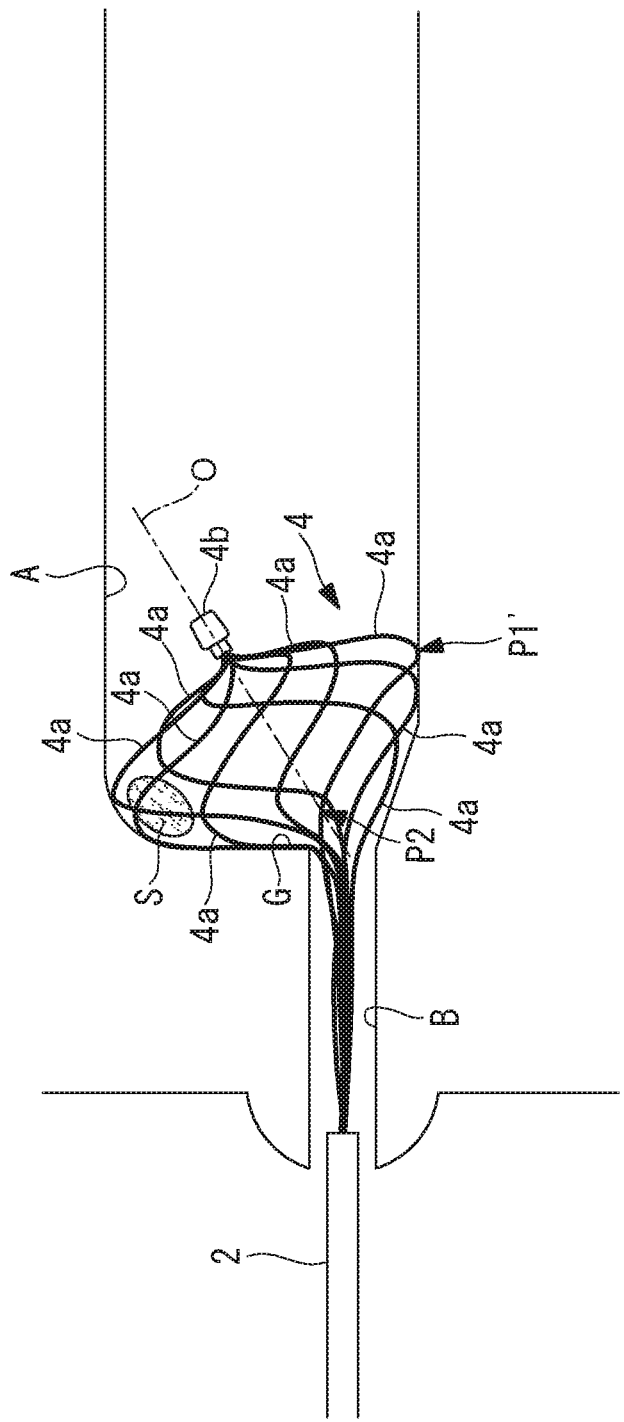

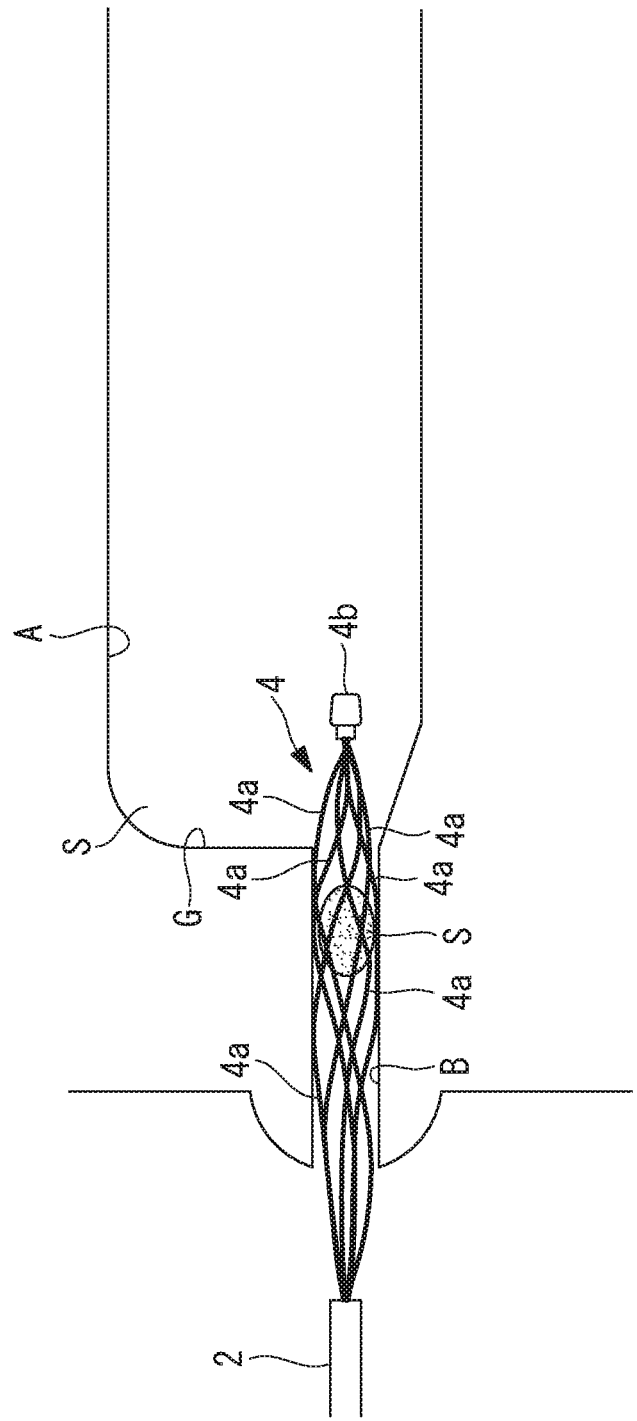

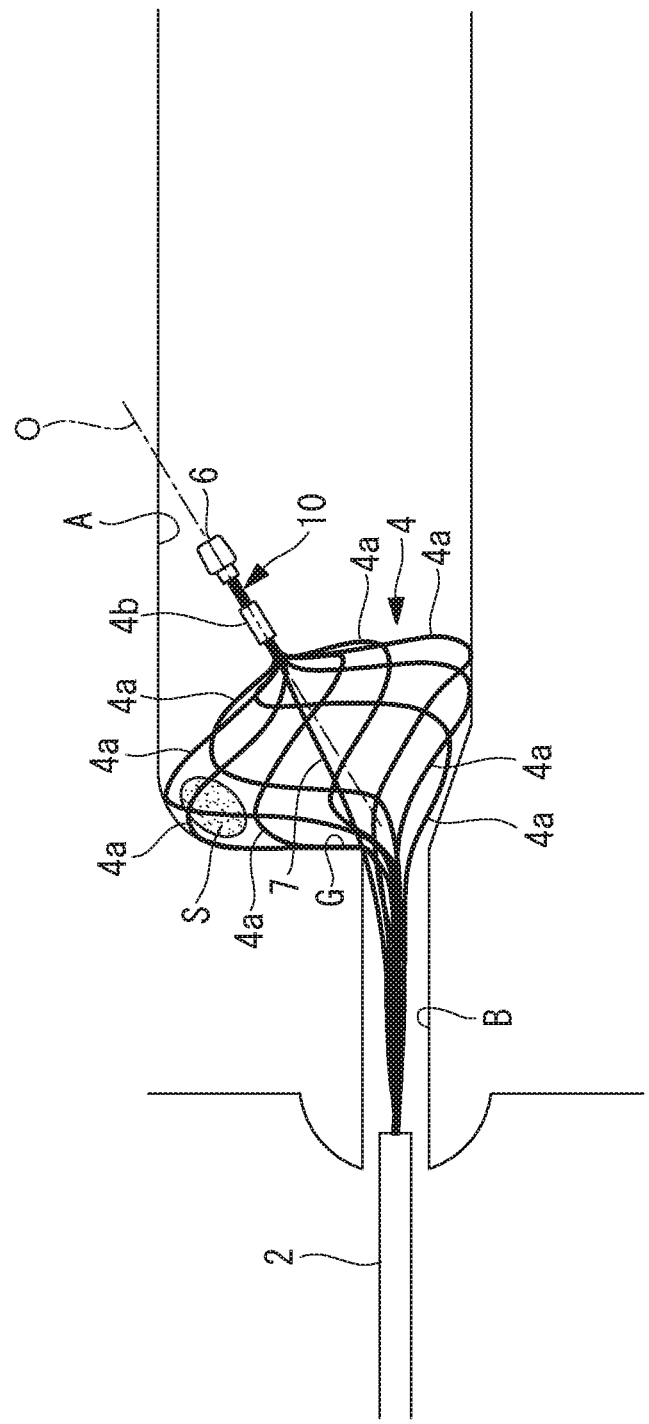

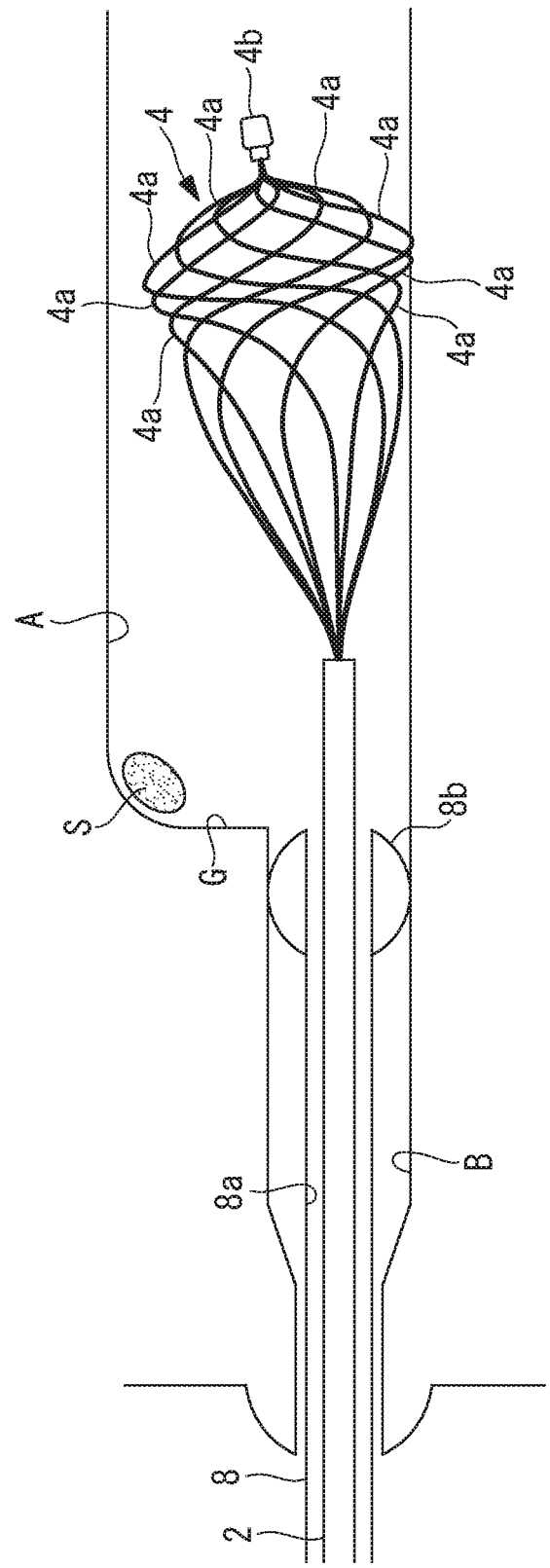

ENDOSCOPE TREATMENT TOOL

CROSS-REFERENCE TO RELATED APPLICATIONS

This is a continuation of International Application PCT/JP2016/054561 which is hereby incorporated by reference herein in its entirety.

TECHNICAL FIELD

The present invention relates to an endoscope treatment tool.

BACKGROUND ART

There are known basket-type gripping forceps with which a gallstone occurring in the bile duct is removed (for example, see Patent Literatures 1 and 2). These basket-type gripping forceps are provided with a basket portion that is formed in a basket shape by bundling a plurality of wires at both ends thereof. The gallstone is picked up by the basket portion, which has been expanded in the bile duct through a gap between wires, and the gallstone is removed from the bile duct by pulling out the entire basket portion from the bile duct.

CITATION LIST

Patent Literature

{PTL 1} Publication of Japanese Patent No. 3075355
{PTL 2} Japanese Examined Patent Application, Publication No. Sho 62-42617

SUMMARY OF INVENTION

An aspect of the present invention is an endoscope treatment tool including: a sheath having a lumen that extends along a longitudinal axis thereof; a basket portion that is configured to protrude from the lumen of the sheath and that is formed of at least one elastic wire; and a manipulation wire that causes the basket portion to be moved forward and backward in a longitudinal direction of the sheath, wherein the at least one elastic wire has a maximum-outer-diameter portion between a distal end of the elastic wire and a proximal end of the elastic wire, and a largest portion that, between the maximum-outer-diameter portion and the proximal end of the elastic wire, reaches a maximum size in an opposite direction from the maximum-outer-diameter portion in a side view from a direction that is orthogonal to a perpendicular line drawn to a center axis of the basket portion from the maximum-outer-diameter portion, and wherein, in a front view of the basket portion, the largest portion is positioned on an opposite side from the side of the maximum-outer-diameter portion with respect to a straight line that is orthogonal to the perpendicular line on the center axis.

BRIEF DESCRIPTION OF DRAWINGS

FIG. 12A is a diagram showing a state in which the basket portion of the endoscope treatment tool in FIG. 1 is expanded in the bile duct.

FIG. 12C is a diagram showing a state in which the basket portion in FIG. 12B is pulled out of the bile duct up to the largest portion, thus capturing a gallstone.

FIG. 12D is a diagram showing a state in which the basket portion is pulled out of the bile duct from the state in FIG. 12C

FIG. 14B is a diagram showing a state in which the basket portion in FIG. 14A is pulled out of the bile duct up to the largest portion, thus capturing a gallstone.

FIG. 18A is a diagram for explaining treatment for removing a gallstone by using the endoscope treatment tool in FIG. 17.

DESCRIPTION OF EMBODIMENT

An endoscope treatment tool 1 according to an embodiment of the present invention will be described below with reference to the drawings.

Figure 1:
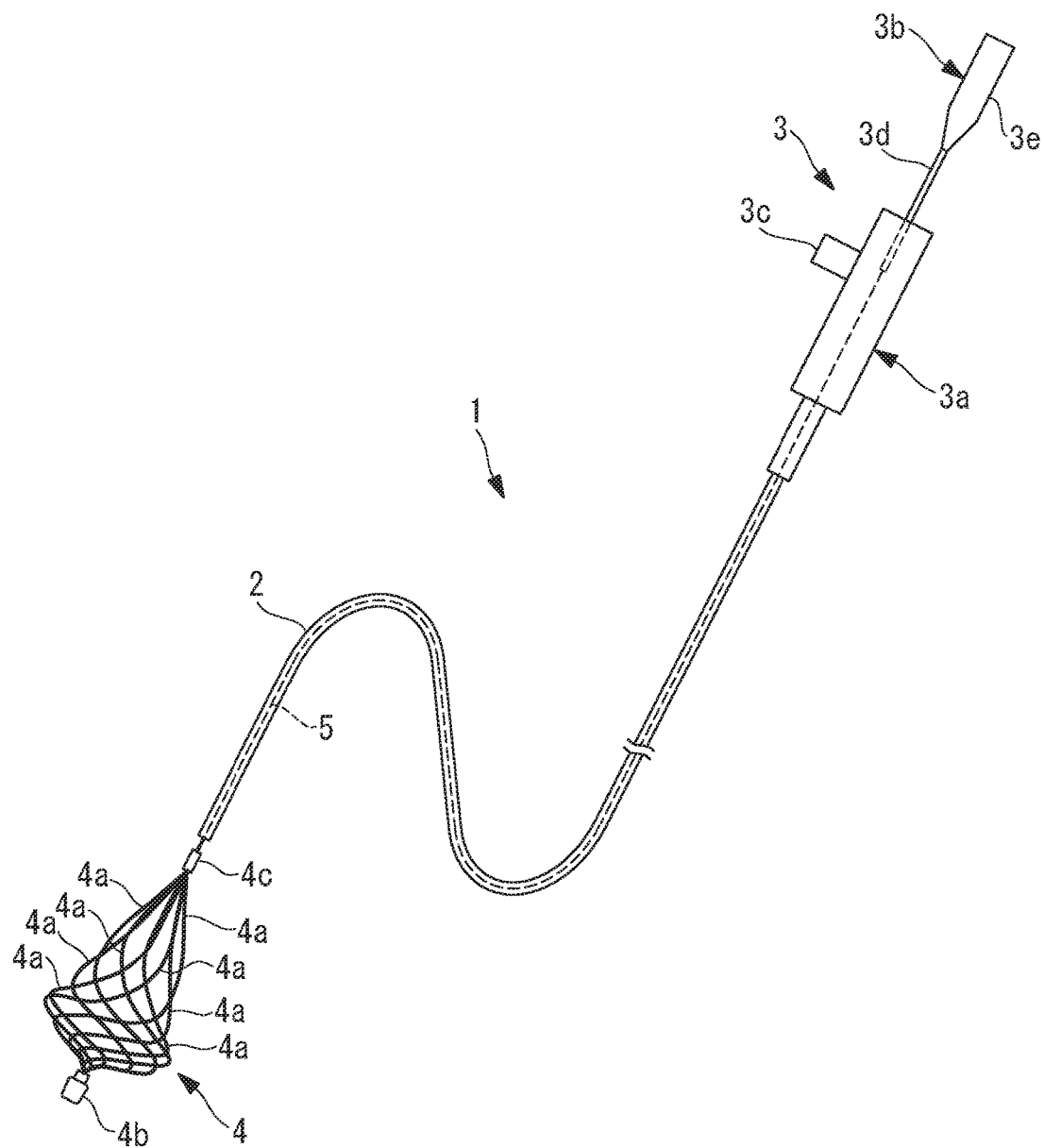
FIG. 1 is an overall configuration diagram showing an endoscope treatment tool according to an embodiment of the present invention.

The endoscope treatment tool 1 according to this embodiment is a treatment tool that is introduced into a body via an endoscope channel (not shown). The endoscope treatment tool 1 is provided with, as shown in FIGS. 1 and 2: an elongated sheath 2 possessing flexibility; a manipulating portion 3 that is provided on a proximal-end side of the sheath 2; a basket portion 4 that is disposed on a distal-end side of the sheath 2; and a manipulation wire 5 that causes the basket portion 4 to be moved forward and backward in a longitudinal direction of the sheath 2 by means of manipulation of the manipulating portion 3.

Figure 2:
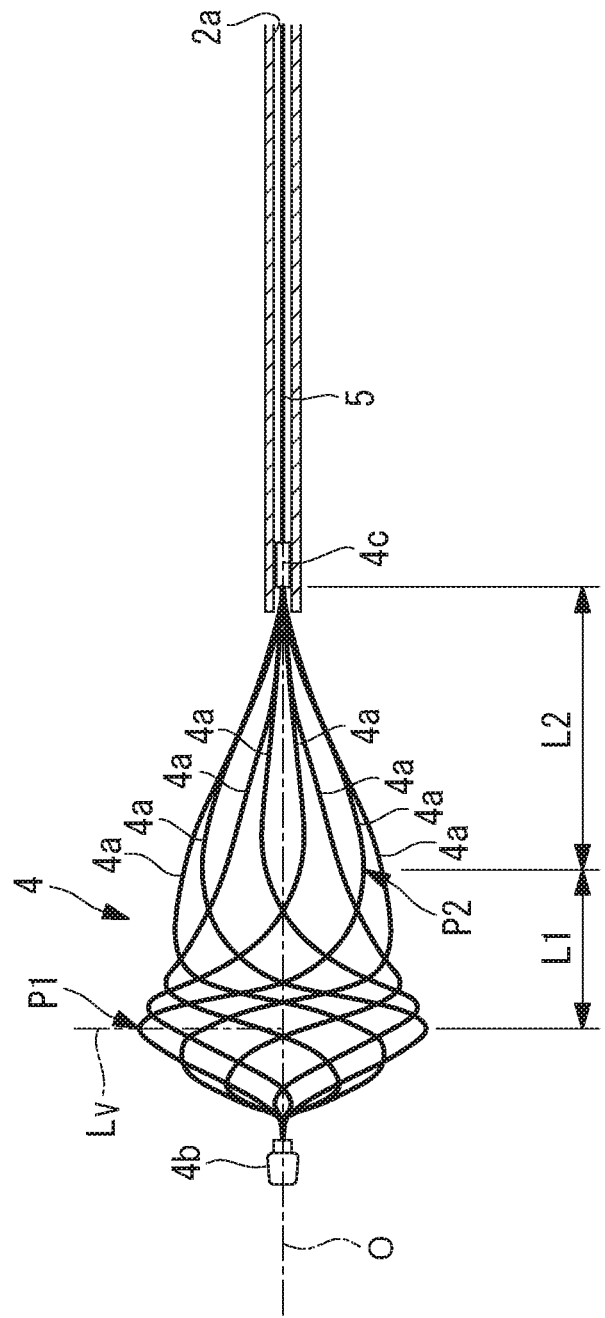
FIG. 2 is a longitudinal cross-sectional view showing an expanded form of a basket portion of the endoscope treatment tool in FIG. 1.

The sheath 2 has an outer diameter that allows insertion thereof into the endoscope channel, and is provided with, as shown in FIG. 2, a lumen 2a that passes therethrough in the longitudinal direction thereof. As the material for the sheath 2, it is possible to employ, for example, a publically known resin material, such as a fluorine resin, a thermoplastic elastomer, or the like, a coil sheath in which a metal material is wound therearound, a blade using a metal wire, or the like by selecting or combining these materials, as appropriate.

The manipulating portion 3 is provided with a manipulating-portion main body 3a and a slider 3b that is movable in the longitudinal direction of the sheath 2 with respect to the manipulating-portion main body 3a. In the figure, reference sign 3c is a liquid feeding port that is provided in the manipulating-portion main body 3a and that communicates with the lumen 2a in the sheath 2. The liquid feeding port 3c is configured so that it is possible to connect a syringe or a pump (not shown) thereto.

The slider 3b is provided with a shaft 3d to which a proximal end of the manipulation wire 5 is secured, and a grip 3e that is secured to the shaft 3d. When an operator grips and pulls the grip 3e toward the proximal end with respect to the manipulating-portion main body 3a, the pulling force is transmitted to the manipulation wire 5, and the basket portion 4 at a distal end of the manipulation wire 5 is moved backward to the proximal end. Conversely, when the operator grips and pushes in the grip 3e toward the distal end with respect to the manipulating-portion main body 3a, the pushing force toward the distal end is transmitted to the manipulation wire 5, and the basket portion 4 at the distal end of the manipulation wire 5 is moved forward to the distal end.

Figure 3:
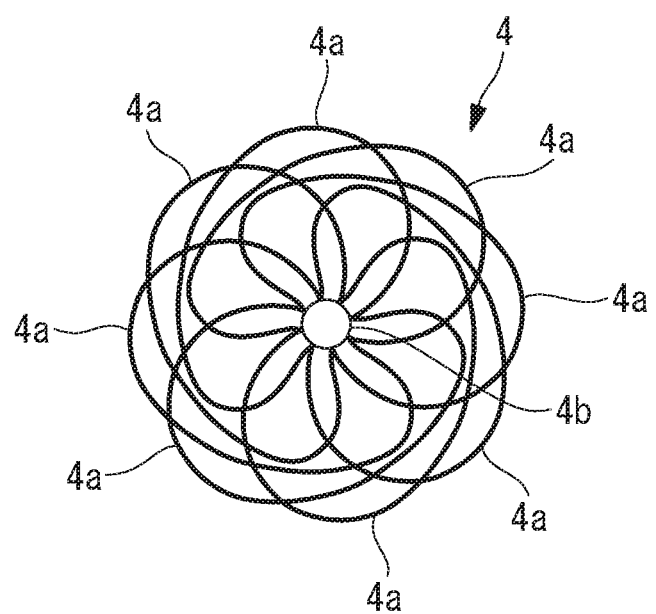
FIG. 3 is a front view viewed from a direction along a center axis of the basket portion in FIG. 2.

As shown in FIGS. 2 and 3, the basket portion 4 is formed in a basket shape by binding a plurality of elastic wires 4a, which are arranged with gaps therebetween in a circumferential direction, at both ends (distal ends and the proximal ends) thereof by means of a distal-end binding portion 4b and a proximal-end binding portion 4c so as to allow contraction and expansion thereof in the radial direction. In other words, it is possible to allow the basket portion 4 to transition between a contracted form and an expanded form.

Figure 4:
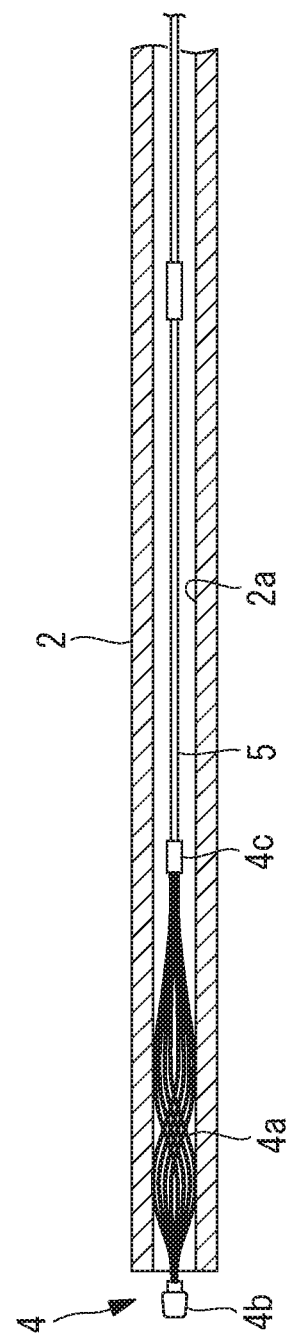
FIG. 4 is a longitudinal cross-sectional view showing a contracted form of the basket portion of the endoscope treatment tool in FIG. 1.

In the contracted form, as shown in FIG. 4, the basket portion 4 is contracted in the radial direction so as to be capable of being accommodated in the lumen 2a in the sheath 2. In the expanded form, as shown in FIG. 2, the basket portion 4 protrudes forward from a distal-end opening of the lumen 2a and is expanded radially outward by an elastic force (restoring force) in a state in which an external force that causes the diameter of the basket portion 4 to decrease is not acting thereon.

Each of the elastic wires 4a that constitute the basket portion 4 is formed of a material having a high elasticity, such as a super elastic alloy or the like, in the form of a single wire or a stranded wire. Examples of the super elastic alloy include a nickel-titanium alloy.

Figure 5:
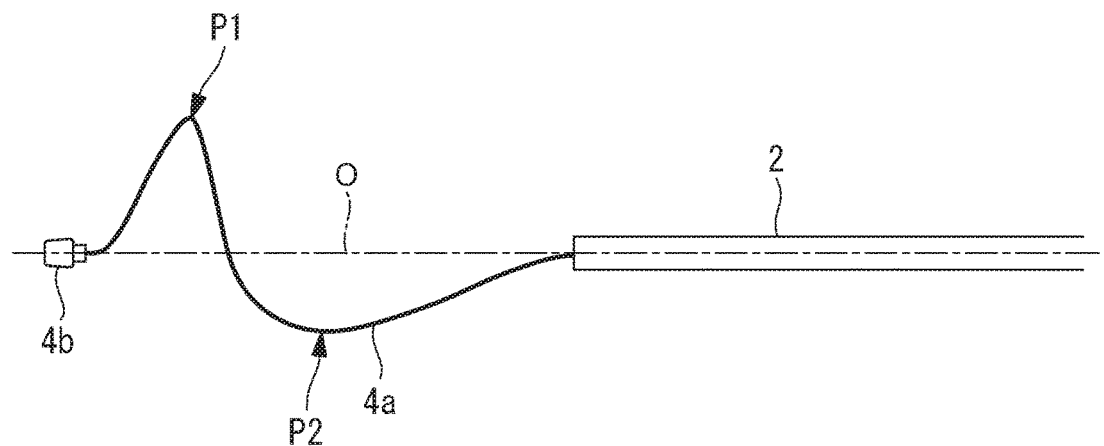
FIG. 5 is a side view for explaining the shape of an elastic wire, the side view being orthogonal to a perpendicular line drawn from a maximum-outer-diameter portion of the basket portion in FIG. 2 to the center axis of the basket portion.
Figure 6:
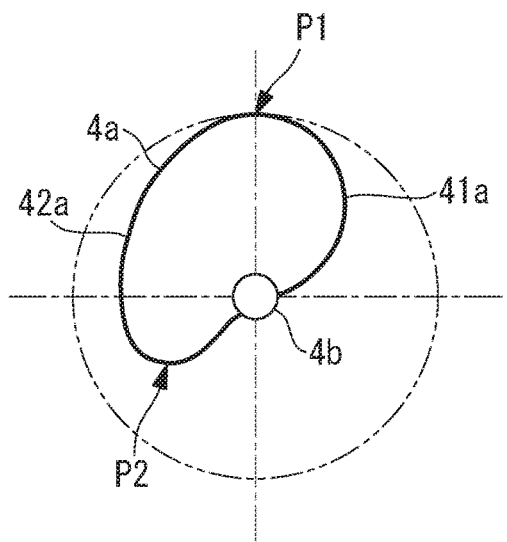
FIG. 6 is a front view showing the shape of the elastic wire in FIG. 5.

In this embodiment, as shown in FIGS. 2 and 6, the basket portion 4 has, between the distal end and the proximal end of at least one elastic wire 4a, a maximum-outer-diameter portion P1 at which the outer diameter of the basket portion 4 reaches a maximum. The maximum-outer-diameter portion P1 is positioned close to the distal end of the basket portion 4. In addition, in FIG. 2, in a side view that is orthogonal to a perpendicular line Lv drawn to a center axis O of the basket portion 4 from the maximum-outer-diameter portion P1, as shown in FIG. 5, one elastic wire 4a has a largest portion P2 that reaches a maximum size in an opposite direction from the maximum-outer-diameter portion P1.

Figure 7A:
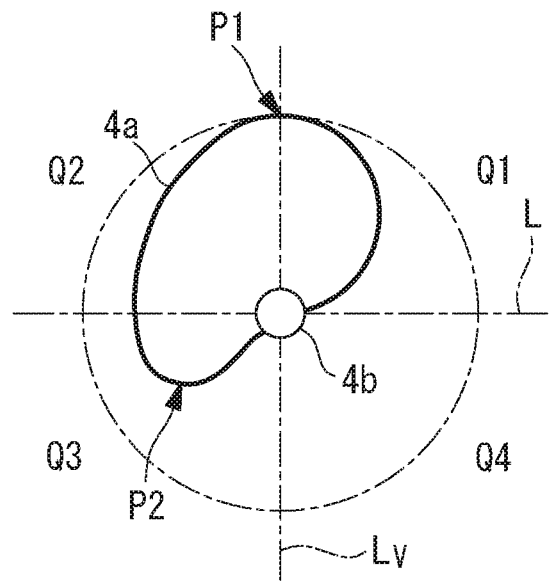
FIG. 7A is a front view for explaining the positional relationship between the maximum-outer-diameter portion and the largest portion of the basket portion in FIG. 5.

The largest portion P2 is located, between the maximum-outer-diameter portion P1 and the proximal end of the elastic wire 4a, at a position toward the proximal end at a certain distance away from the maximum-outer-diameter portion P1. Furthermore, as shown in FIG. 7A, in a front view viewed from the distal-end binding portion 4b in a direction along the center axis O of the basket portion 4, the elastic wire 4a extends from the maximum-outer-diameter portion P1 to the largest portion P2 by crossing a straight line L that is orthogonal to the above-described perpendicular line Lv on the center axis O (the center of the distal-end binding portion 4b).

In other words, in the above-described front view, the largest portion P2 is positioned on the opposite side from the maximum-outer-diameter portion P1 side with respect to the straight line L. Note that, more preferably, in the above-described front view, when the maximum-outer-diameter portion P1 is positioned in the first quadrant Q1 (including the boundary with the second quadrant Q2) in a rectangular coordinate system defined by the two straight lines (the straight line L and the perpendicular line Lv) that are orthogonal to the center axis O, the largest portion P2 is preferably positioned in the third quadrant Q3.

As shown in FIG. 6, the single elastic wire 4a has a first portion 41a that extends to the maximum-outer-diameter portion P1 from the distal end of the elastic wire 4a, and a second portion 42a that extends to the largest portion P2 by being connected to the first portion 41a. The diameter at the first portion 41a increases when approaching the maximum-outer-diameter portion P1 from the distal end of the elastic wire 4a. The diameter at the second portion 42a decreases when approaching the largest portion P2 from the maximum-outer-diameter portion P1. Note that, as shown in FIGS. 5 and 6, it is preferable that the first portion 41a and the second portion 42a be also bent in the above-described side view and front view. In addition, as shown in FIG. 5, in the above-described side view, between the distal end and proximal end of the elastic wire 4a, one elastic wire 4a is bent in a substantially S-shape, and the maximum-outerdiameter portion P1 and the largest portion P2 thereof protrude in opposite directions with respect to the center axis O.

Figure 8:
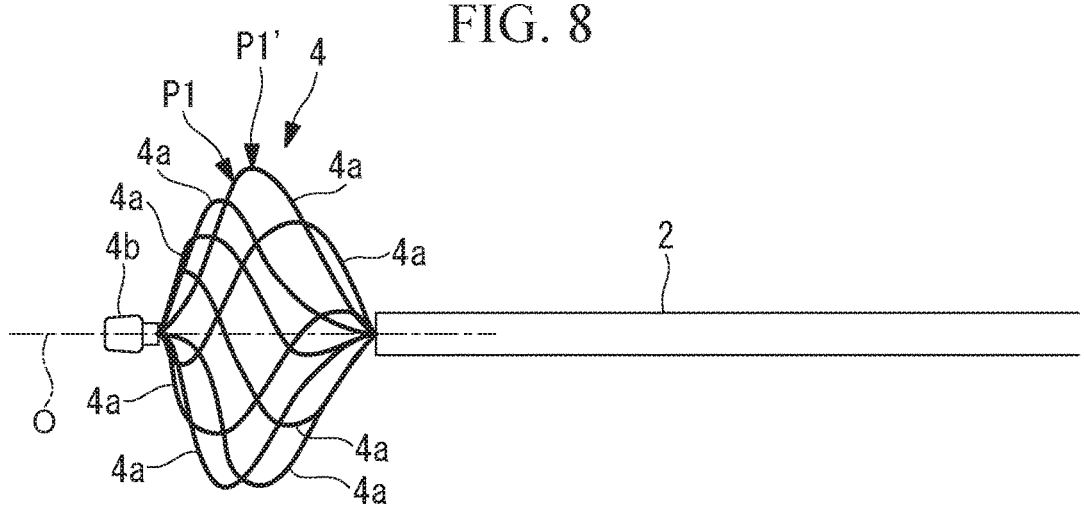
FIG. 8 is a side view showing a state in which the basket portion in FIG. 2 is accommodated in a sheath up to the largest portion thereof.
Figure 9:
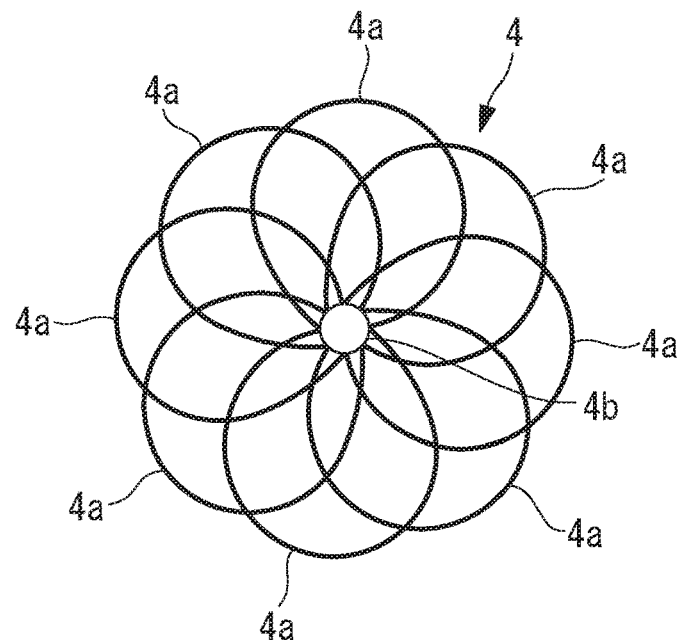
FIG. 9 is a front view of the basket portion in FIG. 8.

As shown in FIGS. 8 and 9, with the above-described basket portion 4, by partially accommodating the proximal end (portion closer to the proximal end than the second portion 42a is) of the basket portion 4 in the sheath 2, the largest portion P2 is brought closer to the center axis O of the basket portion 4. When the largest portion P2 is completely accommodated in the sheath 2, a portion of the second portion 42a (wire extending between the maximum-outer-diameter portion P1 and the largest portion P2) reaches an outer diameter P1' that is greater than that of the maximum-outer-diameter portion P1.

In this embodiment, a plurality of the above-described elastic wires 4a are arranged in the circumferential direction. In addition, as shown in FIG. 3, the largest portions P2 of the plurality of elastic wires 4a are displaced from each other in the circumferential direction. Furthermore, as shown in FIG. 2, in the basket portion 4, it is preferable that a length L1, in the direction along the center axis O, between the maximum-outer-diameter portion P1 and the largest portion P2 be less than a length L2, in the direction along the center axis O, between the largest portion P2 and the proximal end of the elastic wire 4a.

Figure 7B:
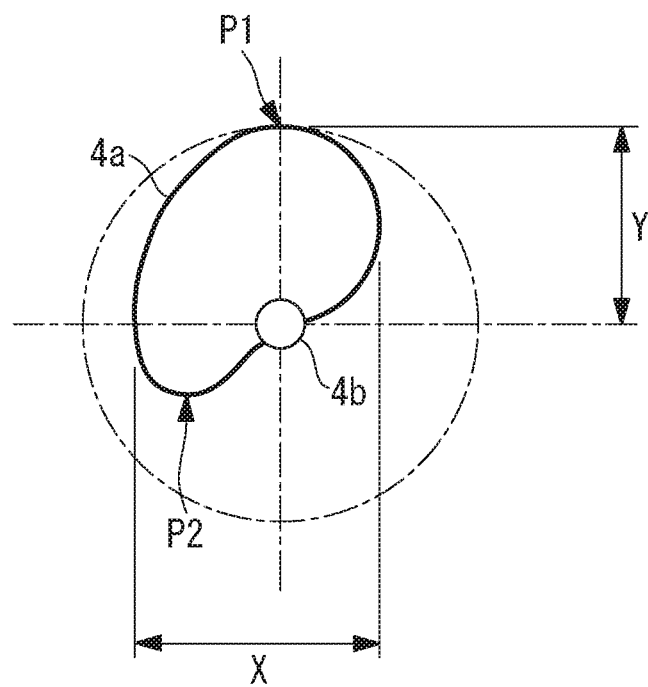
FIG. 7B is a front view showing dimensions in one embodiment of the elastic wire in FIG. 6.

In this embodiment, in the above-described front view, as shown in FIG. 7B, the length of the elastic wire 4a is set so that a width X in the direction in which the straight line L of the basket portion 4 extends (axial direction of the straight line L) is greater than a distance Y between the center axis O and the maximum-outer-diameter portion P1. In this case, as shown in FIG. 3, in the above-described front view, there are many portions in which the individual elastic wires 4a overlap with each other, and thus, the sizes of the inter-wire gaps among the individual elastic wires 4a decrease. Accordingly, it is possible to capture a small calculus by using the basket portion 4 without allowing the calculus to escape therefrom.

Figure 7C:
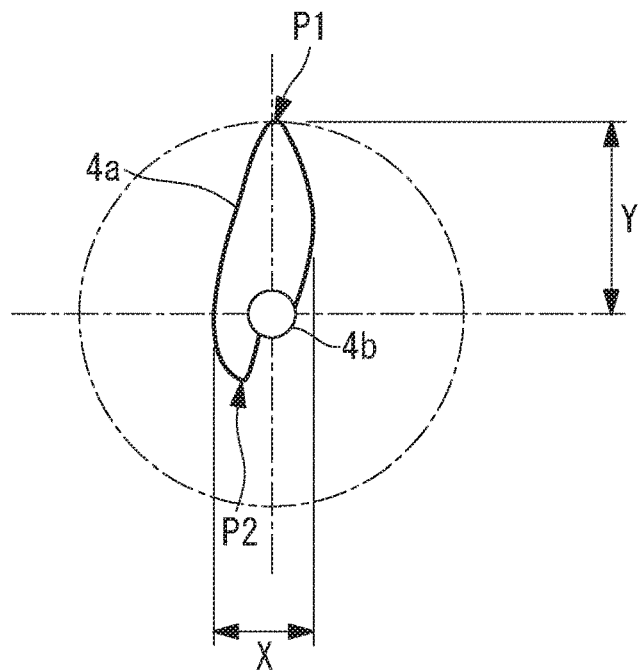
FIG. 7C is a front view showing the dimensions in a modification of the elastic wire in FIG. 6.
Figure 7D:
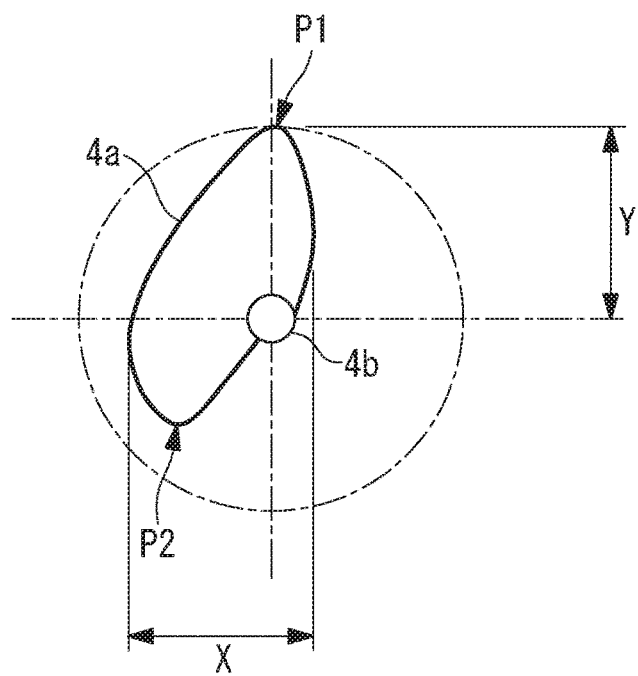
FIG. 7D is a front view showing the dimensions in another modification of the elastic wire in FIG. 6.

Note that, as a modification of this embodiment, the width X may be set to be less than the distance Y in the elastic wire 4a, as shown in FIG. 7C. In this case, because the sizes of the inter-wire gaps among the individual elastic wires 4a increase, it is easier to pick up a large calculus by using the basket portion 4. In addition, as another modification, the width X and the distance Y in the elastic wire 4a may be substantially equal to each other, as shown in FIG. 7D, in consideration of the size of a calculus to be picked up.

In this embodiment, as shown in FIGS. 3 and 6, in the front view viewed from the distal-end binding portion 4b in the direction along the center axis O of the basket portion 4, the individual elastic wires 4a are wound in such a way that the outer diameter decreases counterclockwise. Note that, without limitation thereto, the individual elastic wires 4a may be wound in such a way that the outer diameter decreases clockwise. It is preferable that the individual elastic wires 4a be wound in a circumferential direction over the distal ends to the proximal ends thereof, and that the number of turns thereof be less than one.

Note that, the individual elastic wires 4a may have a helical shape in which the individual elastic wires 4a are wound in the same direction over the entire lengths thereof.

In this case, as shown in FIGS. 2 and 5, the individual elastic wires 4a are formed in a helical manner wherein the diameter of the elastic wires 4a monotonically increases toward the maximum-outer-diameter portion P1 from the distal-end binding portion 4b and monotonically decreases toward the largest portion P2 from the maximum-outer-diameter portion P1.

The plurality of elastic wires 4a positioned between the maximum-outer-diameter portion P1 of the basket portion 4 and the proximal-end binding portion 4c thereof form a pick-up portion in which, so as to make it easier to pick up a calculus or the like, winding pitches of the elastic wires 4a are large and gaps between the adjacent elastic wires 4a are large.

In addition, the plurality of elastic wires 4a positioned between the maximum-outer-diameter portion P1 and the distal-end binding portion 4b form a capturing portion in which winding pitches of the elastic wires 4a are smaller and gaps between the adjacent elastic wires 4a are smaller, as compared to the plurality of elastic wires 4a positioned between the maximum-outer-diameter portion P1 of the basket portion 4 and the proximal-end binding portion 4c thereof, so that the calculus picked up by the basket portion 4 is less likely to fall out therefrom.

Figure 7E:
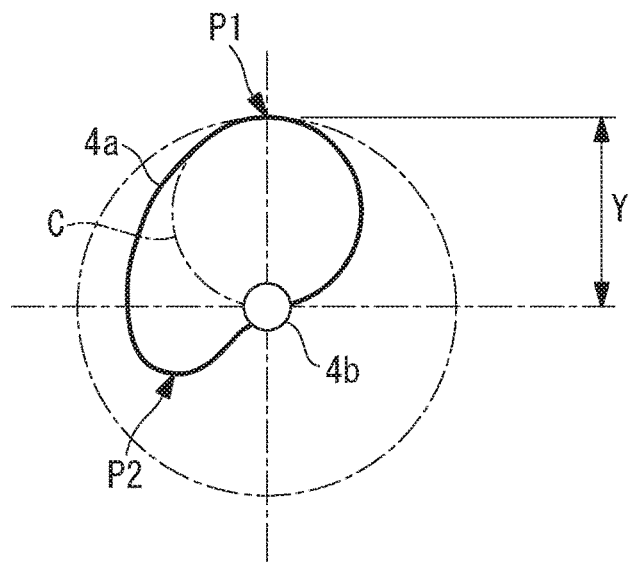
FIG. 7E is a front view for explaining the dimensions in an embodiment of the elastic wire in FIG. 6.

In addition, as shown in FIG. 7E, in the above-described front view, it is preferable that, in each of the elastic wires 4a, the length between the maximum-outer-diameter portion P1 and the largest portion P2 be greater than half a circumferential length of a virtual circle C whose diameter is the distance Y between the center axis O of the basket portion 4 and the maximum-outer-diameter portion P1 thereof. In other words, when the elastic wire 4a is projected from a direction along the center axis O with respect to a virtual plane that is orthogonal to the center axis O, the length between the maximum-outer-diameter portion P1 and the largest portion P2 is greater than half the circumferential length of the virtual circle C.

Note that, as shown in FIG. 7E, in the above-described front view, in each of the elastic wires 4a, the length between the distal-end binding portion 4b and the largest portion P2 may be greater than the circumferential length of the virtual circle C whose diameter is the distance Y between the center axis O of the basket portion 4 and the maximum-outer-diameter portion P1 thereof. In other words, when the elastic wire 4a is projected from a direction along the center axis O with respect to the virtual plane that is orthogonal to the center axis O, the length between the distal-end binding portion 4b and the largest portion P2 is greater than the circumferential length of the virtual circle C.

Figure 10:
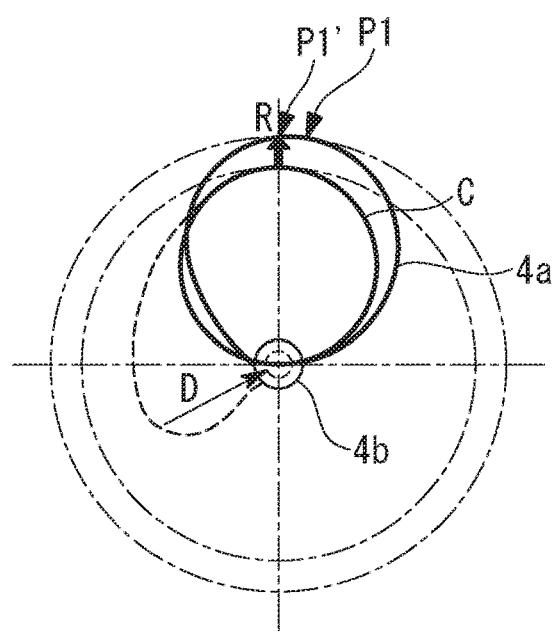
FIG. 10 is a front view showing the elastic wire that constitutes the basket portion in FIG. 9, comparing the state thereof in FIG. 6 and the state thereof in FIG. 8.

By doing so, as shown in FIGS. 8 and 9, when the largest portion P2 contracts radially inward and the largest portion P2 is moved to a position at which the center axis O is substantially reached by partially accommodating the proximal end of the basket portion 4 in the sheath 2, as shown in FIG. 10, the individual elastic wires 4a that constitute the basket portion 4 form rings having diameters that are greater than the diameter Y of the virtual circle C.

As a result, as indicated by arrow D in FIG. 10, when the largest portion P2 contracts radially inward, the portion in each of the elastic wires 4a that forms the maximum-outer-diameter portion P1 and that is disposed between the distal-end binding portion 4b and the largest portion P2 is moved radially farther outward than the virtual circle C is, as indicated by arrow R. In other words, the maximum-outer-diameter portion P1 of the basket portion 4 expands radially outward.

Figure 11A:
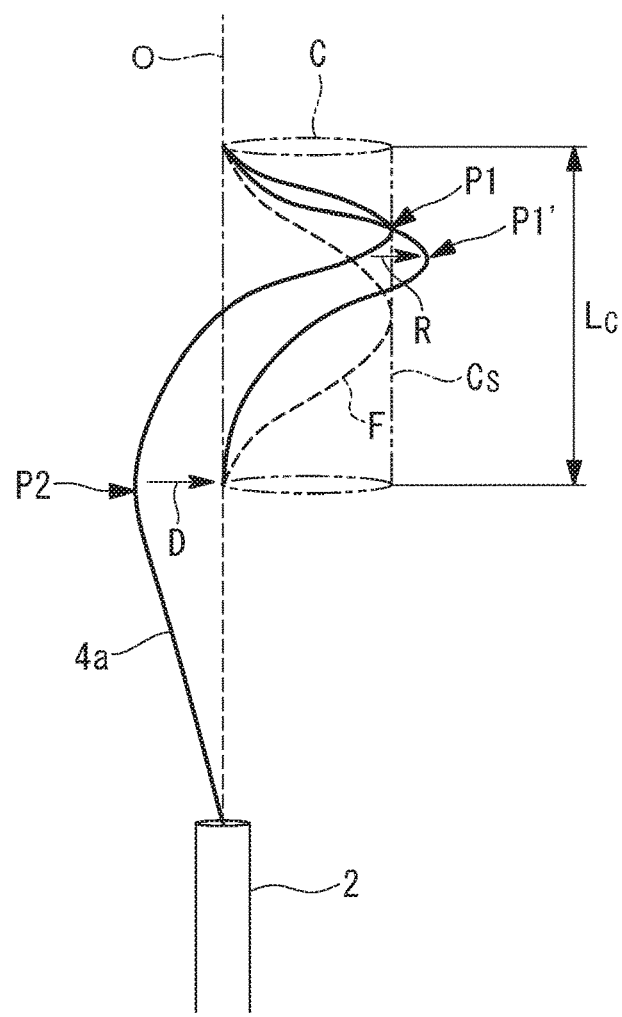
FIG. 11A is a side view for explaining, using an alternative description, the operation of the basket portion in FIG. 10
Figure 11B:
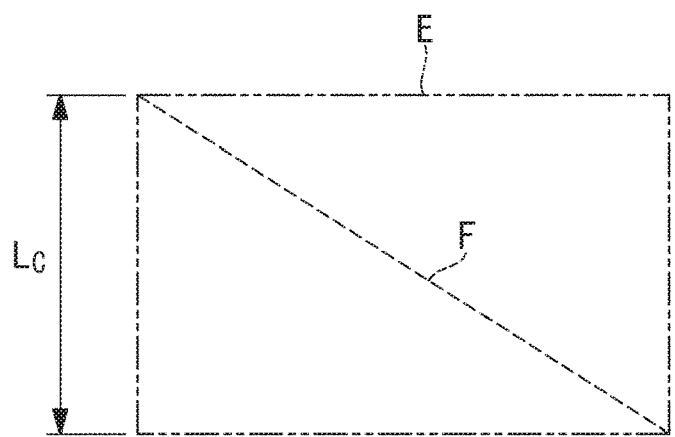
FIG. 11B is an expanded view in which a virtual cylindrical surface in FIG. 11A is opened up.

In other words, as shown in FIG. 11A, when a virtual cylindrical surface Cs is assumed, in which the above-described virtual circle C forms a bottom surface thereof and a distance Lc in the direction along the center axis O between the distal-end binding portion 4b and the largest portion P2 is the height thereof, with each of the elastic wires 4a, the actual length between the distal-end binding portion 4b and the largest portion P2 is greater than the length of a diagonal F in a rectangle E formed by opening up the virtual cylindrical surface Cs, as shown in FIG. 11B.

The length of the diagonal F of the above-described rectangle E is the length of the elastic wire 4a when being wound around the above-described virtual cylindrical surface Cs in a helical manner without gaps. In this embodiment, the actual length between the distal-end binding portion 4b and the largest portion P2 is greater than the length of the above-described diagonal F of the rectangle E. Therefore, as indicated by arrow D in FIG. 11A, when the largest portion P2 contracts radially inward and the largest portion P2 is moved to the position at which it substantially reaches center axis O, as indicated by arrow R, the elastic wire 4a is moved radially outward with respect to the virtual cylindrical surface Cs.

As a result, because, in each of the elastic wires 4a, the portion that forms the maximum-outer-diameter portion P1 and that is disposed between the distal-end binding portion 4b and the largest portion P2 is moved radially farther outward than the virtual circle C is, the maximum-outer-diameter portion P1 of the basket portion 4 expands radially outward.

The operation of the thus-configured endoscope treatment tool 1 according to this embodiment will be described below.

A case in which a gallstone S in a bile duct A is captured by using the endoscope treatment tool 1 according to this embodiment will be described, wherein a small gallstone S is present in a stepped portion G formed in a lopsided manner at a boundary between the bile duct A and a duodenal papilla B, as shown in FIGS. 12A to 12D.

As shown in FIG. 4, the basket portion 4, in the contracted state, is accommodated in the sheath 2, and the sheath 2 is inserted, from the distal end thereof, into the bile duct A from the duodenal papilla B via an endoscope channel inserted into the duodenum. In this state, by moving the slider 3b of the manipulating portion 3 forward, a pressing force is applied to the manipulation wire 5, and thus, the basket portion 4 protrudes from the opening of the lumen 2a at the distal end of the sheath 2.

By being released in a large area in the bile duct A, the basket portion 4 is restored into the expanded state by an elastic restoring force, and takes the basket-like form having the maximum-outer-diameter portion P1 and the largest portion P2. Because the bile duct A is larger on the stepped portion G side and is smaller on the opposite side, as shown in FIG. 12A, the basket portion 4 restored to the expanded state is placed in a state in which the basket portion 4 is apart from an inner wall of the bile duct A on the stepped portion G side and is brought into contact with an inner wall of the bile duct A on the opposite side.

Figure 12B:
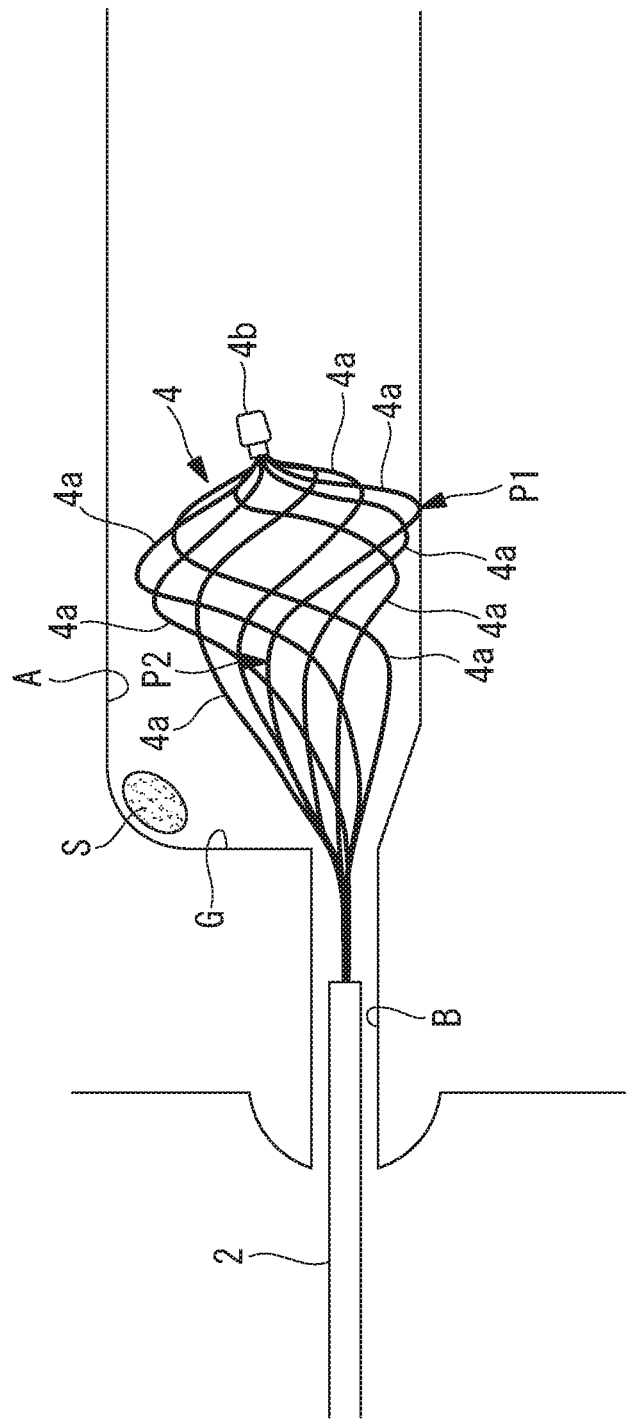
FIG. 12B is a diagram showing a state in which a portion of the basket portion in FIG. 12A is pulled out of the bile duct.

From this state, by pulling the sheath 2 toward the proximal end, the basket portion 4 is moved toward the proximal end in the bile duct A. By doing so, as shown in FIG. 12B, the proximal end of the basket portion 4 is pulled into a narrow pathway of the duodenal papilla B, and thus, the basket portion 4 is gradually contracted radially inward from the proximal end thereof.

Specifically, by partially pulling the proximal end (portion closer to the proximal end than the second portion 42a is) of the basket portion 4 into a narrow pathway of the duodenal papilla B, the proximal end of the basket portion 4 receives an external force from the papilla B, and thus, the largest portion P2 is brought closer to the center axis O of the basket portion 4.

When the largest portion P2 is brought closer to the center axis O of the basket portion 4, the second portion 42a (wire that extends between the maximum-outer-diameter portion P1 and the largest portion P2) applies a force in a direction in which the straight line L is crossed so as to further increase the maximum outer diameter of the basket portion 4. A portion of the second portion 42a is deformed so that the outer diameter becomes greater than that of the maximum-outer-diameter portion P1 before the diameter increases, as shown in FIGS. 8, 9, and 12C.

As a result, as shown in FIG. 12C, when the basket portion 4 is pulled into the narrow pathway of the duodenal papilla B up to the vicinity of the largest portion P2, as with the state in FIG. 8, the largest portion P2 contracts and the maximum-outer-diameter portion P1 expands radially outward. Thus, the outer diameter P1', which is greater than that of the maximum-outer-diameter portion P1, is formed by the portion of the second portion 42a (wire that extends between the maximum-outer-diameter portion P1 and the largest portion P2).

Because of this, the basket portion 4 is tilted toward the stepped portion G by receiving a reaction force from the inner wall of the bile duct A on the opposite side from the stepped portion G. In other words, due to the increase in the diameter at the maximum-outer-diameter portion P1 and tilting of the basket portion 4 as a whole, as shown in FIG. 12C, the basket portion 4 is placed so that it is possible to reach the small gallstone S that is present in the stepped portion G. Accordingly, it is possible to accommodate the gallstone S in the basket portion 4 from the gaps between the elastic wires 4a, and, as shown in FIG. 12D, by further pulling the sheath 2, it is possible to remove the gallstone S from the bile duct A.

Note that, as shown in FIG. 2, in the basket portion 4, the length L1 in the direction along the center axis O between the maximum-outer-diameter portion P1 and the largest portion P2 is less than the length L2 in the center axis O direction between the largest portion P2 and the proximal end of the elastic wire 4a. Because of this, before the elastic wire 4a reaches the gallstone S that has gotten into the stepped portion G, it is unlikely for the second portion 42a to receive an external force from the papilla B, and thus, the maximum outer diameter of the basket portion 4 does not decrease.

In addition, in the process of increasing the maximum outer diameter of the basket portion 4, in the largest portions P2 of the plurality of elastic wires 4a, the outer diameters at the respective largest portions P2 decrease while being maintained in a state in which the largest portions P2 are displaced in the circumferential direction with respect to each other.

As has been described above, with the endoscope treatment tool 1 according to this embodiment, there is an advantage in that it is possible to more reliably capture and remove even a gallstone S that is present in the stepped portion G formed in a lopsided manner at the boundary between the bile duct A and the duodenal papilla B.

Figure 13:
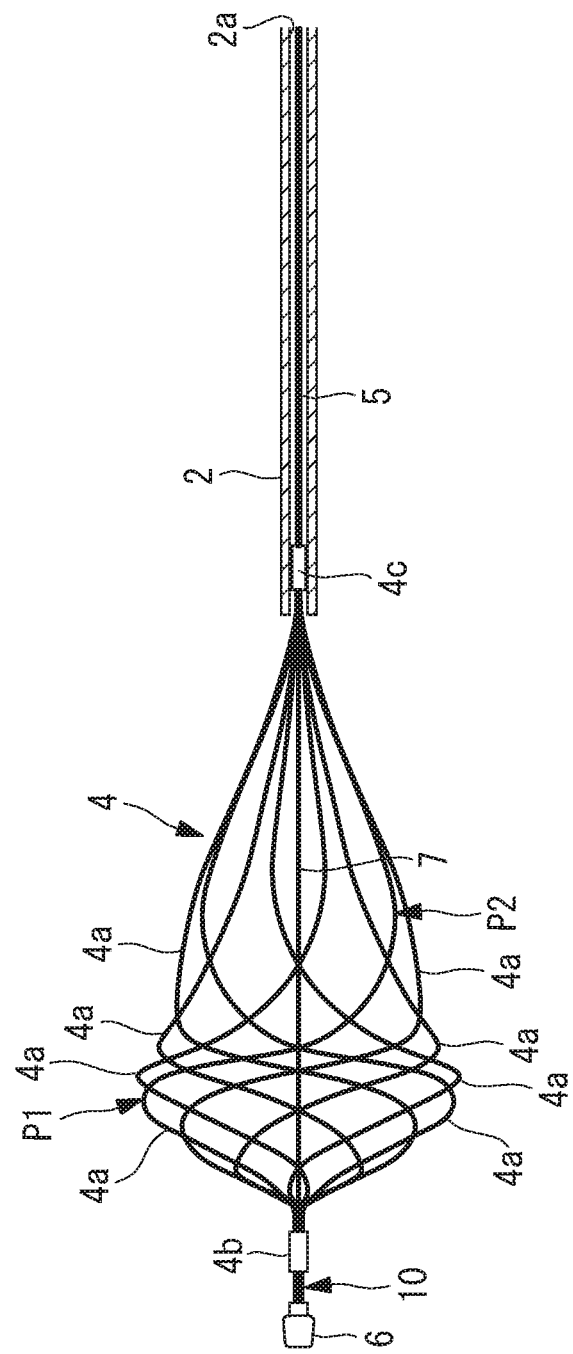
FIG. 13 is a side view showing a modification of the basket portion in FIG. 2.
Figure 14A:
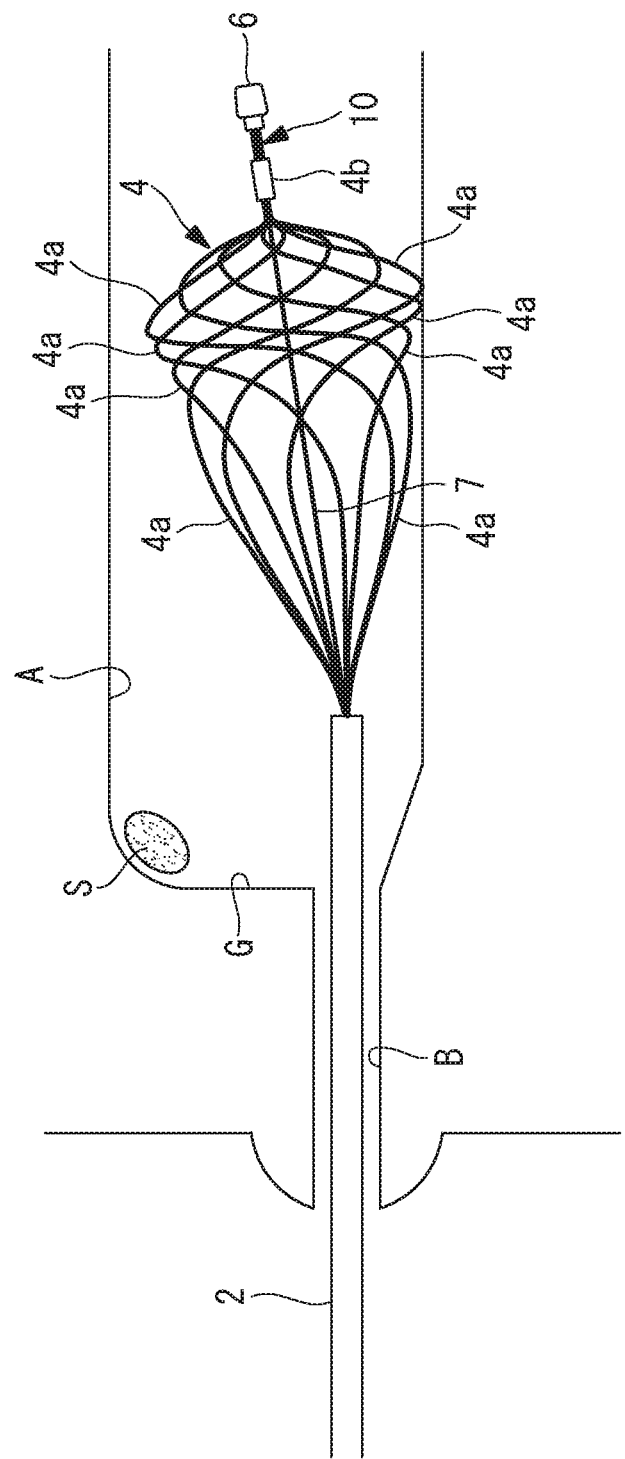
FIG. 14A is a diagram showing a state in which the basket portion in FIG. 13 is expanded in the bile duct.

Note that, in this embodiment, as shown in FIG. 13, a distal-end tip 6 may be provided at a distal end that is farther out than the distal-end binding portion 4b is, and a support member 7 that has passed through the basket portion 4 and in which at least a portion thereof is inserted into the sheath 2 may be secured to the distal-end tip 6. The support member 7 has a greater rigidity than the elastic wires 4a, and is capable of supporting the basket portion 4, thus holding the shape thereof. In addition, as shown in FIGS. 14A and 14B, when the basket portion 4 is pressed by the inner wall of the bile duct A, it is possible to tilt the basket portion 4 by bending the support member 7 toward the stepped portion G.

As shown in FIG. 13, it is preferable that the support member 7 be disposed at a position displaced from the center axis O of the basket portion 4.

By doing so, when the gallstone S is captured by the basket portion 4, by pushing off the support member 7 radially outward with respect to the center axis O, it is possible to dispose the gallstone S in the vicinity of the center axis O of the basket portion 4. Because the sizes of the gaps between the elastic wires 4a decrease in the basket portion 4 on the distal-end side or the proximal-end side thereof where the elastic wires 4a are gathered near the center axis O, by disposing the gallstone S in the vicinity of the center axis O, it is possible to reduce the possibility of losing the gallstone S from the basket portion 4.

In addition, as shown in FIG. 13, a joint portion 10 that extends farther toward the distal end of the basket portion 4 from the distal-end binding portion 4b may be provided, and the support member 7 may be secured to the joint portion 10. By deforming the joint portion 10, it is possible to facilitate an additional movement of the support member 7 from the center axis O of the basket portion 4.

Figure 15:
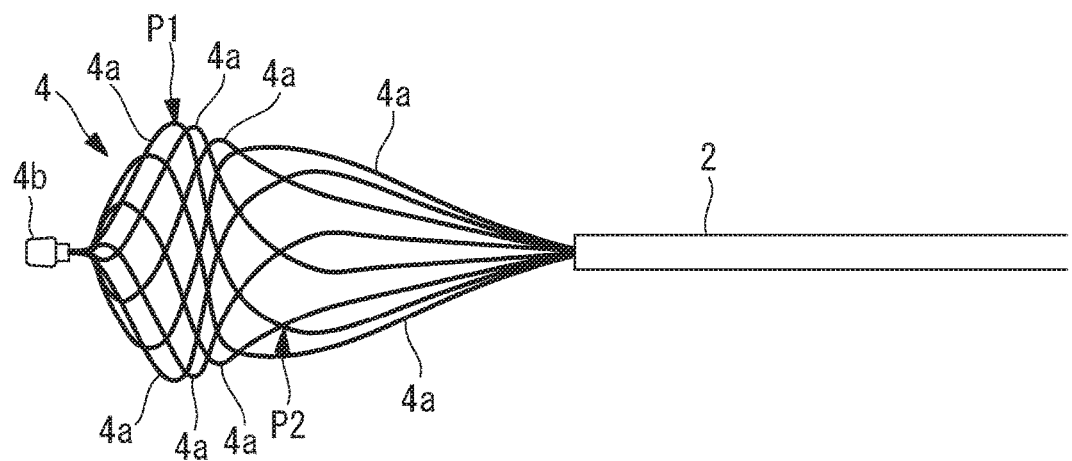
FIG. 15 is a side view showing a modification of the basket portion in FIG. 2.
Figure 16:
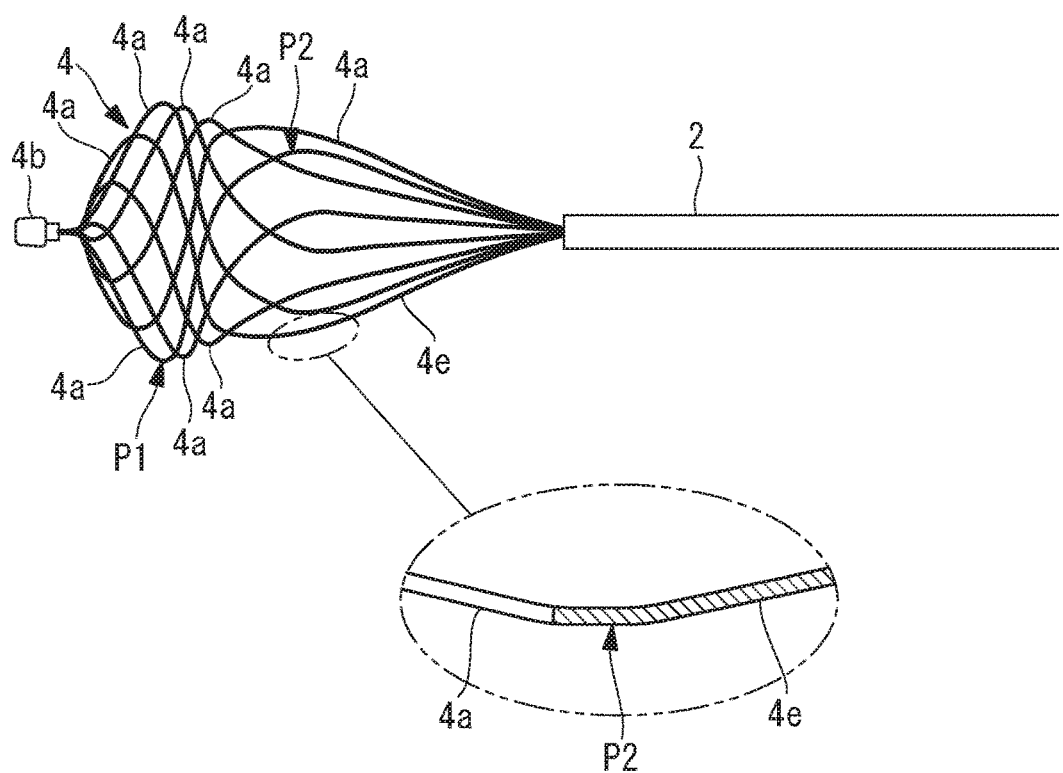
FIG. 16 is a diagram showing a modification of the basket portion in FIG. 15, in which a joining portion is enlarged.

In addition, in this embodiment, as the individual elastic wires 4a that constitute the basket portion 4, those that are bent in helical shapes over the entire lengths thereof have been described as examples; however, alternatively, as shown in FIG. 15, elastic wires 4a having folds at the largest portions P2 may be employed. In addition, in this case, as shown in FIG. 16, the elastic wires 4a having the helical shapes and the elastic wires 4e having the folds may be joined together slightly farther on the distal-end side than the largest portions P2 are. Because it is difficult to form folds with a super elastic material formed of nickel titanium or the like, it is preferable that the elastic wires 4e on the proximal-end side be formed of a material with which it is easy to form the folds, such as stainless-steel stranded wires or the like, and that the two types of wires be joined together.

Figure 17:
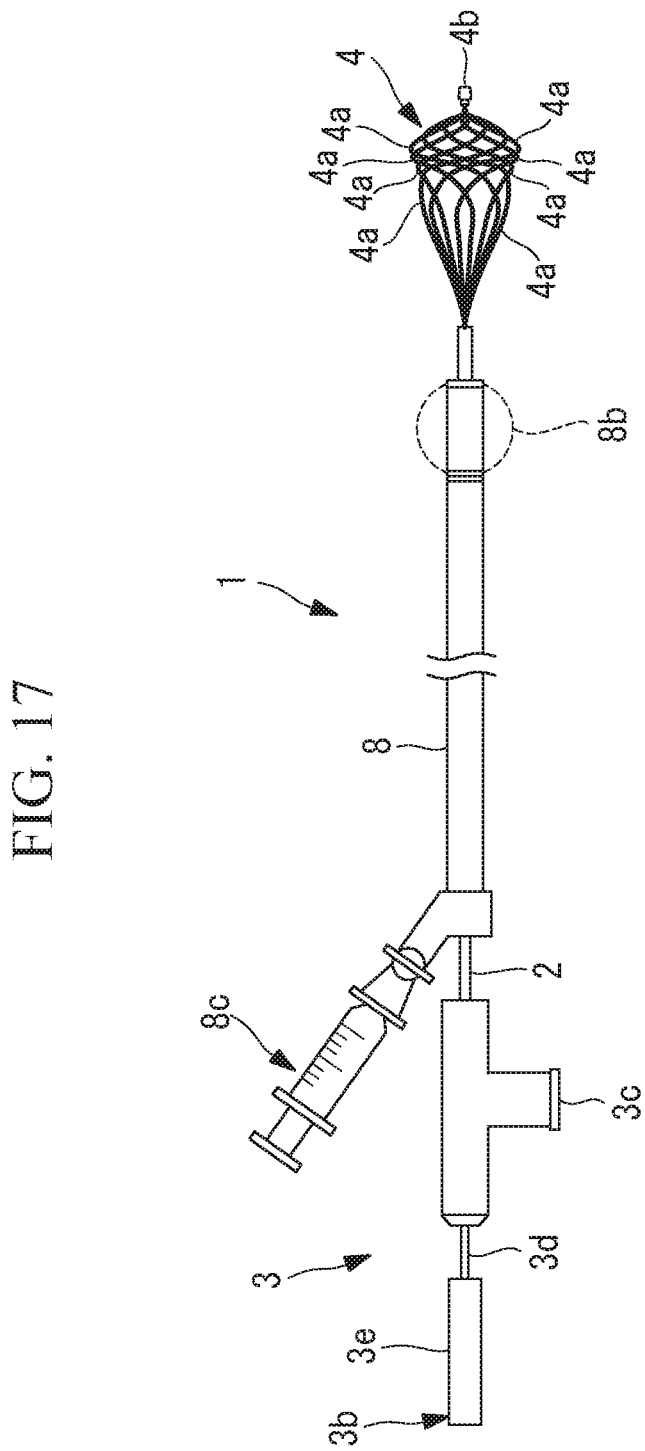
FIG. 17 is an overall configuration diagram showing a modification of the endoscope treatment tool in FIG. 1.

In addition, as a modification of this embodiment, as shown in FIG. 17, an outer sheath 8 that has a lumen 8 through which the sheath 2 passes may additionally be provided, a balloon 8b that expands radially outward may be provided at a distal end of the outer sheath 8, and a gas feeding means 8c, such as a syringe, for supplying a gas for inflating the balloon 8b may be provided at a proximal end of the outer sheath 8.

Figure 18B:
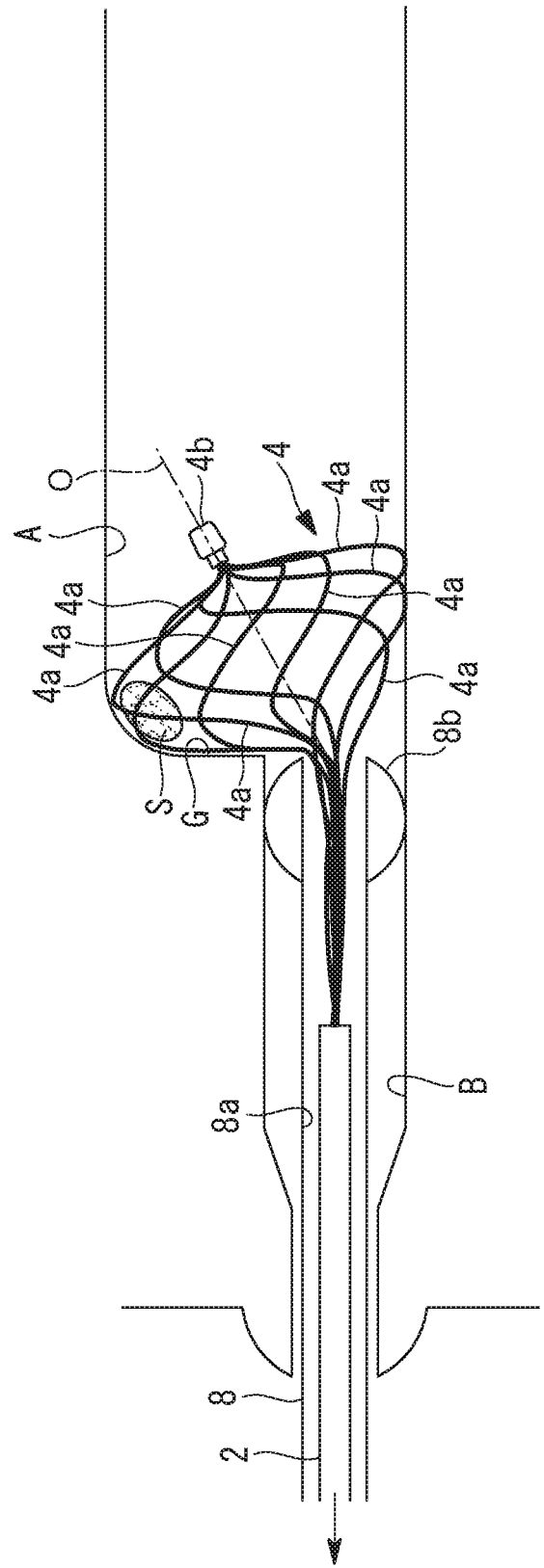
FIG. 18B is a diagram showing a state in which the basket portion is pulled out of the bile duct up to the largest portion from the state in FIG. 18A, thus capturing a gallstone.

By doing so, as shown in FIGS. 18A and 18B, in the case in which the pathway of the duodenal papilla B is expanded at a connecting portion with the bile duct A, it is possible to secure the outer sheath 8 to the pathway of the duodenal papilla B by inflating the balloon 8b. Accordingly, by pulling the basket portion 4 into the lumen 8a of the outer sheath 8 by pulling the sheath 2, it is possible to capture a small gallstone S in the stepped portion G by sufficiently contracting the largest portion P2 of the basket portion 4.

Figure 19:
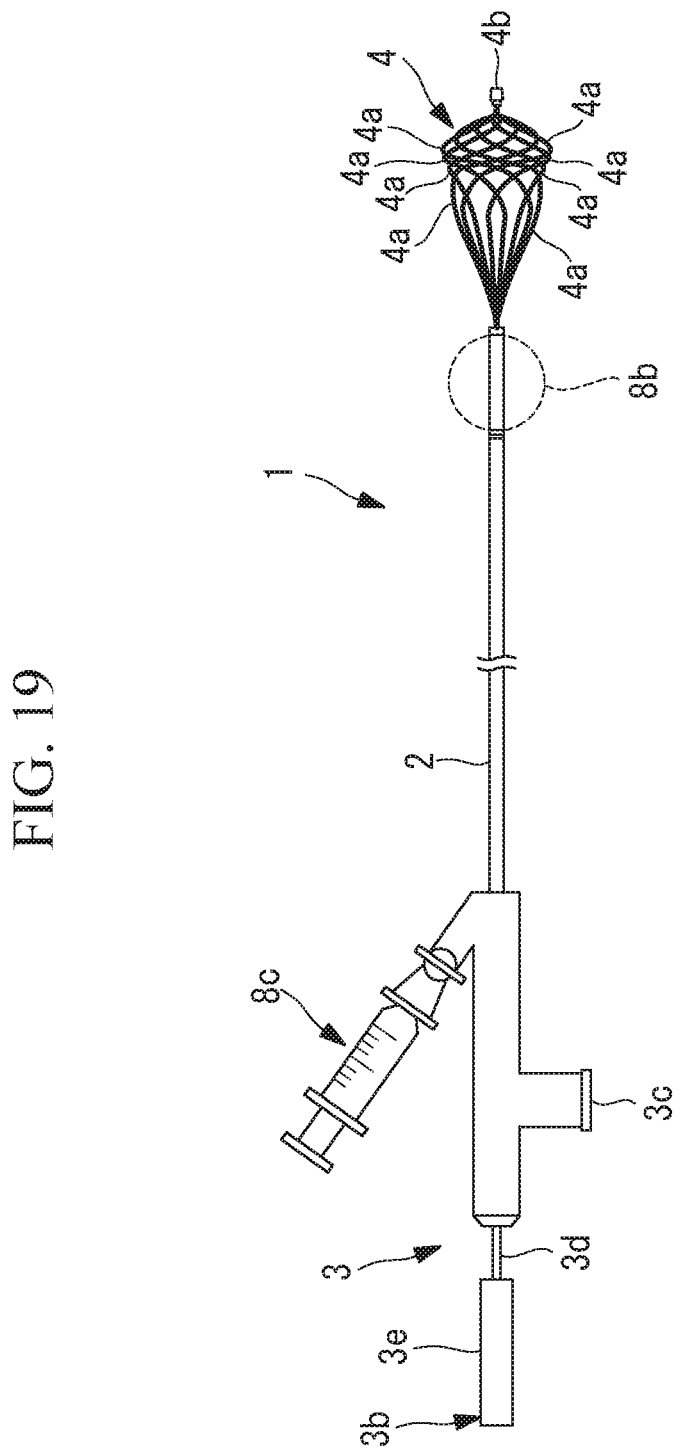
FIG. 19 is an overall configuration diagram showing another modification of the endoscope treatment tool in FIG. 1.

In addition, alternatively, as shown in FIG. 19, the balloon 8b may be provided at the distal end of the sheath 2, and the gas feeding means 8c, such as a syringe, for supplying the gas for inflating the balloon 8b may be provided at the proximal end of the sheath 2.

Figure 20A:
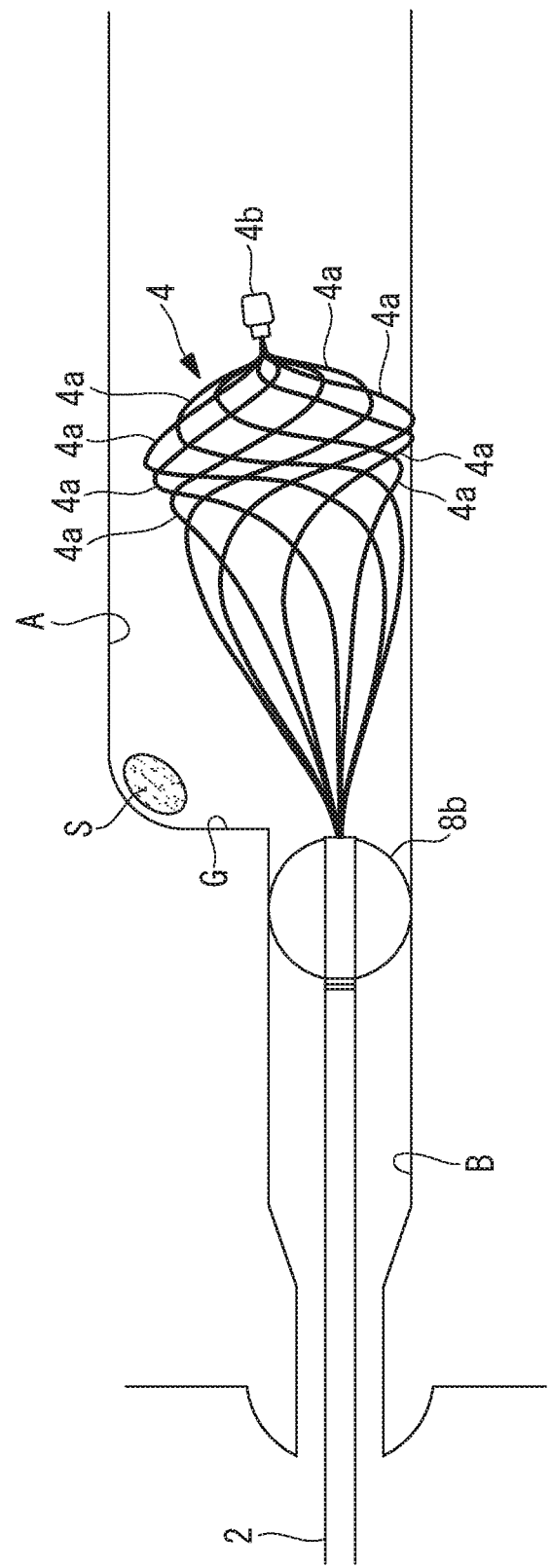
FIG. 20A is a diagram for explaining treatment for removing a gallstone by using the endoscope treatment tool in FIG. 19.
Figure 20B:
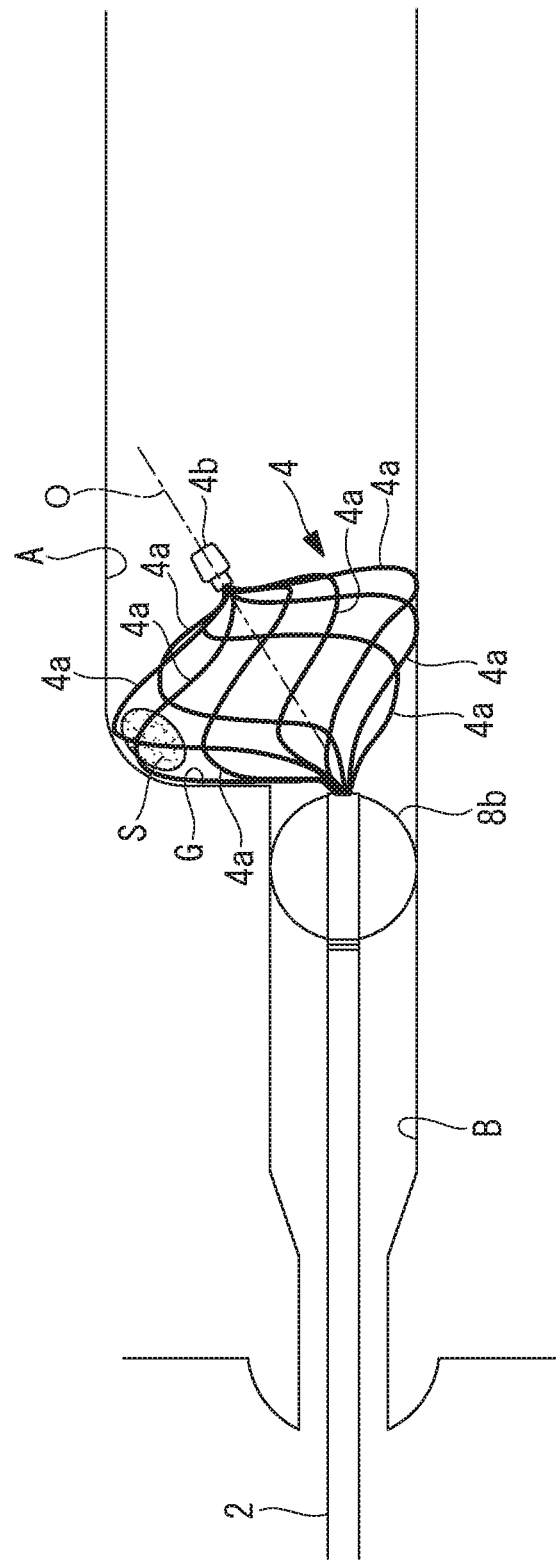
FIG. 20B is a diagram showing a state in which the basket portion is pulled into a sheath up to the largest portion from the state in FIG. 20A, thus capturing the gallstone.

In this case, as shown in FIG. 20A, by securing the distal end of the sheath 2 to the pathway of the duodenal papilla B by inflating the balloon 8b, and, as shown in FIG. 20B, by pulling the basket portion 4 into the sheath 2 by pulling the slider 3b of the manipulating portion 3 toward the proximal end. It is possible to capture a small gallstone S in the stepped portion G by sufficiently contracting the largest portions P2 of the basket portion 4.

The above-described embodiment leads to the following invention.

An aspect of the present invention is an endoscope treatment tool including: a sheath having a lumen that extends along a longitudinal axis thereof; a basket portion that is configured to protrude from the lumen of the sheath and that is formed of at least one elastic wire; and a manipulation wire that causes the basket portion to be moved forward and backward in a longitudinal direction of the sheath, wherein the at least one elastic wire has a maximum-outer-diameter portion between a distal end of the elastic wire and a proximal end of the elastic wire, and a largest portion that, between the maximum-outer-diameter portion and the proximal end of the elastic wire, reaches a maximum size in an opposite direction from the maximum-outer-diameter portion in a side view from a direction that is orthogonal to a perpendicular line drawn to a center axis of the basket portion from the maximum-outer-diameter portion, and wherein, in a front view of the basket portion, the largest portion is positioned on an opposite side from the side of the maximum-outer-diameter portion with respect to a straight line that is orthogonal to the perpendicular line on the center axis.

In the above-described aspect, in the basket portion, a length in a direction along the center axis between the maximum-outer-diameter portion and the largest portion may be less than a length in the direction along the center axis between the largest portion and the proximal end of the elastic wire.

In addition, in the above-described aspect, with the at least one elastic wire, when the largest portion is brought close to the center axis, a portion of a region between the maximum-outer-diameter portion and the largest portion may have a greater outer diameter than the maximum-outer-diameter portion.

In addition, in the above-described aspect, in the front view, when the maximum-outer-diameter portion is positioned in a first quadrant in a rectangular coordinate system defined by two straight lines that are orthogonal to the center axis, the largest portion may be positioned in a third quadrant thereof.

In addition, in the above-described aspect, in the front view, a width of the basket portion in a direction in which the straight line extends and a distance between the center axis and the maximum-outer-diameter portion may be substantially equal to each other.

In addition, in the above-described aspect, in the front view, a width of the basket portion in a direction in which the straight line extends may be greater than a distance between the center axis and the maximum-outer-diameter portion.

In addition, in the above-described aspect, in the front view, a width of the basket portion in a direction in which the straight line extends may be less than a distance between the center axis and the maximum-outer-diameter portion.

In addition, in the above-described aspect, the maximum-outer-diameter portion may be positioned on a distal-end side of the basket portion, the at least one elastic wire may have a first portion that extends from the distal end of the elastic wire to the maximum-outer-diameter portion and a second portion that extends to the largest portion by being connected to the first portion, a diameter at the first portion may increase toward the maximum-outer-diameter portion from the elastic wire, and a diameter at the second portion may decrease toward the largest portion from the maximum-outer-diameter portion.

In addition, in the above-described aspect, the at least one elastic wire may be wound in a circumferential direction from the distal end to the proximal end of the elastic wire and the number of turns of the elastic wire may be less than one.

In addition, in the above-described aspect, in the side view, the first portion and the second portion may be bent.

In addition, in the above-described aspect, in the front view, the first portion and the second portion may be bent.

In addition, in the above-described aspect, the at least one elastic wire may comprise a plurality of elastic wires that are arranged in a circumferential direction, and the largest portions of the plurality of elastic wires may be displaced in the circumferential direction from each other.

In addition, in the above-described aspect, wherein the basket portion may be formed by binding two ends of the plurality of elastic wires by using a distal-end binding portion and a proximal-end binding portion, and the basket portion may have a shape in which the plurality of elastic wires are bent so that a maximum outer diameter of the basket portion increases radially outward when a diameter at a portion between the largest portion and the proximal-end binding portion decreases.

In addition, in the above-described aspect, lengths between the distal-end binding portion of the elastic wires and the largest portions may be greater than a circumferential length of a virtual circle in which, in the front view, a distance between the center axis and the maximum-outer-diameter portion is the diameter thereof.

In addition, in the above-described aspect, in the plurality of elastic wires between the distal-end binding portion and the maximum-outer-diameter portion, gaps between adjacent elastic wires may be smaller than those in the plurality of elastic wires between the maximum-outer-diameter portion and the proximal-end binding portion.

In addition, in the above-described aspect, the elastic wires may be formed in a helical manner so that diameters thereof monotonically increase toward the maximum-outer-diameter portion from the distal-end binding portion and so that the diameters thereof monotonically decrease toward the largest portion from the maximum-outer-diameter portion.

In addition, in the above-described aspect, the basket portion may be provided with a support member that is at least partially accommodated in the sheath and that is joined with the distal-end binding portion.

In addition, in the above-described aspect, the support member may be disposed at a position that is displaced from the center axis of the basket portion.

In addition, the above-described aspect may be provided with a joint portion that extends farther out toward a distal end of the basket portion from the distal-end binding portion, where the support member may be secured to the joint portion.

REFERENCE SIGNS LIST 1 endoscope treatment tool
2 sheath
2a lumen
4 basket portion
4a elastic wire
4b distal-end binding portion
4c proximal-end binding portion
5 manipulation wire
7 support member
10 joint portion P1 maximum-outer-diameter portion
P2 largest portion

The invention claimed is:
1. An endoscope treatment tool comprising:
a sheath having a lumen that extends along a longitudinal axis thereof;
a basket portion that is configured to protrude from the lumen of the sheath and that is formed of at least one elastic wire;
a support member that is inserted into the sheath and in which a distal end thereof is secured to a distal end of the basket portion; and
a manipulation wire that causes the basket portion to be moved forward and backward in a longitudinal direction of the sheath,
wherein, in a state in which a region of the basket portion between a proximal end of the at least one elastic wire and a largest portion of the at least one elastic wire protrudes from the sheath, the at least one elastic wire has
a maximum-outer-diameter portion between a distal end of the at least one elastic wire and the proximal end of the at least one elastic wire, and
the largest portion, between the maximum-outer-diameter portion and the proximal end of the at least one elastic wire, reaches a maximum size in an opposite direction from the maximum-outer-diameter portion in a side view from a direction that is orthogonal to a perpendicular line drawn to a center axis of the basket portion from the maximum-outer-diameter portion,
wherein, in a front view of the basket portion, the largest portion is positioned on an opposite side from the side of the maximum-outer-diameter portion with respect to a straight line that is orthogonal to the perpendicular line,
wherein, in a state in which the region of the basket portion is accommodated in the sheath, an outer diameter of a portion of the at least one elastic wire between the maximum-outer-diameter portion and the largest portion becomes greater than that of the maximum-outer-diameter portion, and
wherein the support member is configured so that, when the maximum-outer-diameter portion is pressed by a wall of a duct and its diameter is increased, the center axis is tilted with respect to the longitudinal axis of the sheath by bending the support member, the support member having a greater rigidity than the at least one elastic wire.

2. An endoscope treatment tool according to claim 1, wherein, in the basket portion, a length in a direction along the center axis between the maximum-outer-diameter portion and the largest portion is less than a length in the direction along the center axis between the largest portion and the proximal end of the at least one elastic wire.

3. An endoscope treatment tool according to claim 1, wherein, in the front view, when the maximum-outer-diameter portion is positioned in a first quadrant in a rectangular coordinate system defined by two straight lines that are orthogonal to the center axis, the largest portion is positioned in a third quadrant thereof.

4. An endoscope treatment tool according to claim 1, wherein, in the front view, a width of the basket portion in a direction in which the straight line extends and a distance between the center axis and the maximum-outer-diameter portion are substantially equal to each other.

5. An endoscope treatment tool according to claim 1, wherein, in the front view, a width of the basket portion in a direction in which the straight line extends is greater than a distance between the center axis and the maximum-outer-diameter portion.

6. An endoscope treatment tool according to claim 1, wherein, in the front view, a width of the basket portion in a direction in which the straight line extends is less than a distance between the center axis and the maximum-outer-diameter portion.

7. An endoscope treatment tool according to claim 1,
wherein the maximum-outer-diameter portion is positioned on a distal-end side of the basket portion,
wherein the at least one elastic wire has
a first portion that extends from the distal end of the at least one elastic wire to the maximum-outer-diameter portion, and
a second portion that extends to the largest portion by being connected to the first portion, and
wherein a diameter at the first portion increases toward the maximum-outer-diameter portion from the at least one elastic wire, and a diameter at the second portion decreases toward the largest portion from the maximum-outer-diameter portion.

8. An endoscope treatment tool according to claim 7, wherein the at least one elastic wire is wound in a circumferential direction from the distal end to the proximal end of the at least one elastic wire and the number of turns of the at least one elastic wire is less than one.

9. An endoscope treatment tool according to claim 7, wherein, in the side view, the first portion and the second portion are bent.

10. An endoscope treatment tool according to claim 9, wherein, in the front view, the first portion and the second portion are bent.

11. An endoscope treatment tool according to claim 1,
wherein the at least one elastic wire comprises a plurality of elastic wires that are arranged in a circumferential direction, and
the largest portion of the at least one elastic wire of the plurality of elastic wires is displaced in the circumferential direction from each other largest portion of each elastic wire of the plurality of elastic wires.

12. An endoscope treatment tool according to claim 11,
wherein the basket portion is formed by binding two ends of the plurality of elastic wires by using a distal-end binding portion and a proximal-end binding portion, and
the basket portion has a shape in which the plurality of elastic wires are bent so that a maximum outer diameter of the basket portion increases radially outward when a diameter at a portion between the largest portion and the proximal-end binding portion decreases.

13. An endoscope treatment tool according to claim 12, wherein lengths between the distal-end binding portion of the plurality of elastic wires and the largest portions are greater than a circumferential length of a virtual circle in which, in the front view, a distance between the center axis and the maximum-outer-diameter portion is the diameter of the virtual circle.

14. An endoscope treatment tool according to claim 12, wherein, in the plurality of elastic wires between the distal-end binding portion and the maximum-outer-diameter portion, gaps between adjacent elastic wires are smaller than those in the plurality of elastic wires between the maximum-outer-diameter portion and the proximal-end binding portion.

15. An endoscope treatment tool according to claim 12, wherein the plurality of elastic wires are formed in a helical manner so that diameters thereof monotonically increase toward the maximum-outer-diameter portion from the distal-end binding portion and so that the diameters thereof monotonically decrease toward the largest portion from the maximum-outer-diameter portion.

16. An endoscope treatment tool according to claim 12, wherein the support member is joined with the distal-end binding portion.

17. An endoscope treatment tool according to claim 16, further comprising:
a joint portion that extends farther out toward a distal end of the basket portion from the distal-end binding portion,
wherein the support member is secured to the joint portion.

18. An endoscope treatment tool according to claim 1, wherein the support member is disposed at a position that is displaced from the center axis of the basket portion.

19. An endoscope treatment tool comprising:
a sheath having a lumen that extends along a longitudinal axis thereof;
a basket portion that is configured to protrude from the lumen of the sheath and that is formed of at least one elastic wire
a support member that is inserted into the sheath and in which a distal end thereof is secured to a distal end of the basket portion; and
a manipulation wire that causes the basket portion to be moved forward and backward in a longitudinal direction of the sheath,
wherein, in a state in which a region of the basket portion between a proximal end of the at least one elastic wire and a largest portion of the at least one elastic wire protrudes from the sheath, the at least one elastic wire has
a maximum-outer-diameter portion between a distal end of the at least one elastic wire and the proximal end of the at least one elastic wire, and
the largest portion, between the maximum-outer-diameter portion and the proximal end of the at least one elastic wire, reaches a maximum size in an opposite direction from the maximum-outer-diameter portion in a side view from a direction that is orthogonal to a perpendicular line drawn to a center axis of the basket portion from the maximum-outer-diameter portion,
wherein, in a front view of the basket portion, the largest portion is positioned on an opposite side from the side of the maximum-outer-diameter portion with respect to a straight line that is orthogonal to the perpendicular line on the center axis,
wherein, in a state in which the region of the basket portion is accommodated in a papilla, an outer diameter of a portion of the at least one elastic wire between the maximum-outer-diameter portion and the largest portion becomes greater than that of the maximum-outer-diameter portion, and
wherein the support member is configured so that, when the maximum-outer-diameter portion is pressed by a wall of a bile duct and its diameter is increased, the center axis is tilted with respect to the longitudinal axis of the sheath by bending the support member, the support member having a greater rigidity than the at least one elastic wire.

* * * * *